(12) United States Patent
Wang et al.

(10) Patent No.: US 8,853,338 B2
(45) Date of Patent: *Oct. 7, 2014

(54) CURABLE DENTAL COMPOSITIONS AND ARTICLES COMPRISING POLYMERIZABLE IONIC LIQUIDS

(75) Inventors: Yizhong Wang, Woodbury, MN (US); Joel D. Oxman, Minneapolis, MN (US); Larry R. Krepski, White Bear Lake, MN (US); Peiwang Zhu, Woodbury, MN (US); Kevin M. Lewandowski, Inver Grove Heights, MN (US); Brian N. Holmes, Saint Paul, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/510,991

(22) PCT Filed: Dec. 6, 2010

(86) PCT No.: PCT/US2010/059033
§ 371 (c)(1),
(2), (4) Date: May 21, 2012

(87) PCT Pub. No.: WO2011/087621
PCT Pub. Date: Jul. 21, 2011

(65) Prior Publication Data
US 2012/0276503 A1    Nov. 1, 2012

Related U.S. Application Data

(60) Provisional application No. 61/289,098, filed on Dec. 22, 2009, provisional application No. 61/360,159, filed on Jun. 30, 2010.

(51) Int. Cl.
| | |
|---|---|
| *C08F 26/06* | (2006.01) |
| *A61C 19/06* | (2006.01) |
| *C08F 2/46* | (2006.01) |
| *A61K 6/083* | (2006.01) |
| *C08F 28/02* | (2006.01) |
| *C08F 26/02* | (2006.01) |
| *A61K 6/00* | (2006.01) |

(52) U.S. Cl.
CPC ............ *A61K 6/083* (2013.01); *A61K 6/0023* (2013.01); *A61K 6/0017* (2013.01)
USPC ......... 526/263; 526/287; 526/312; 526/319; 522/167; 522/173; 433/217.1; 523/118

(58) Field of Classification Search
CPC ........... C08F 26/06; C08F 2/46; C08F 28/02; C08F 26/02; A61C 19/06; A61K 6/083
USPC .......... 526/263, 287, 312, 319; 522/167, 173; 433/217.1; 523/118
See application file for complete search history.

(56) References Cited

U.S. PATENT DOCUMENTS

| | | |
|---|---|---|
| 3,250,808 A | 5/1966 | Moore, Jr. |
| 3,780,092 A | 12/1973 | Samour |
| 4,049,705 A | 9/1977 | Schwing |
| 4,262,072 A | 4/1981 | Wendling |
| 4,503,169 A | 3/1985 | Randklev |
| 4,619,979 A | 10/1986 | Kotnour |
| 4,843,134 A | 6/1989 | Kotnour |
| 4,872,936 A | 10/1989 | Engelbrecht |
| 4,933,405 A | 6/1990 | Evani |
| 5,063,257 A | 11/1991 | Akahane |
| 5,130,347 A | 7/1992 | Mitra |
| 5,154,762 A | 10/1992 | Mitra |
| 5,159,035 A | 10/1992 | Evani |
| 5,161,041 A | 11/1992 | Abileah |
| 5,175,030 A | 12/1992 | Lu |
| 5,183,597 A | 2/1993 | Lu |
| 5,227,413 A | 7/1993 | Mitra |
| 5,367,002 A | 11/1994 | Huang |
| 5,427,835 A | 6/1995 | Morrison |
| 5,501,707 A | 3/1996 | Schieferstein |
| 5,501,727 A | 3/1996 | Wang |

(Continued)

FOREIGN PATENT DOCUMENTS

| | | |
|---|---|---|
| DE | 2750030 | 5/1979 |
| EP | 0537774 | 4/1993 |
| EP | 0980682 | 2/2000 |
| EP | 1116769 | 7/2001 |
| EP | 1285947 | 2/2003 |

(Continued)

OTHER PUBLICATIONS

Abedin et al., "Ionic Liquids: The Link to High-Temperature Molten Salts?", Accounts of Chemical Research, 2007, 40, 1106-1113.

(Continued)

*Primary Examiner* — Michael M Bernshteyn
(74) *Attorney, Agent, or Firm* — Carolyn A. Fischer

(57) ABSTRACT

Presently described are curable dental compositions comprising a polymerizable ionic liquid. The polymerizable ionic liquid comprises one or more ethylenically unsaturated (e.g. free-radically polymerizable) groups. Various embodiments of curable dental compositions are described. In some embodiments, the polymerizable ionic liquid is a monofunctional polymerizable ionic liquid comprising an ethylenically unsaturated group. In other embodiments, the polymerizable ionic liquid is a multifunctional polymerizable ionic liquid comprising at least two ethylenically unsaturated groups. The curable dental compositions describe herein can be utilized as dental primers, dental adhesives, dental sealants, and dental composites. In many embodiments, the curable dental compositions further comprise an initiator such as a photoinitiator.

23 Claims, No Drawings

(56) References Cited

U.S. PATENT DOCUMENTS

| | | | |
|---|---|---|---|
| 5,520,725 A | 5/1996 | Kato | |
| 5,534,322 A | 7/1996 | Ueyama | |
| 5,545,676 A | 8/1996 | Palazzotto | |
| 5,626,654 A | 5/1997 | Breton | |
| 5,637,646 A | 6/1997 | Ellis | |
| 5,771,328 A | 6/1998 | Wortman | |
| 5,783,120 A | 7/1998 | Ouderkirk | |
| 5,788,749 A | 8/1998 | Breton | |
| 5,804,610 A | 9/1998 | Hamer | |
| 5,825,543 A | 10/1998 | Ouderkirk | |
| 5,828,488 A | 10/1998 | Ouderkirk | |
| 5,859,089 A | 1/1999 | Qian | |
| 5,871,360 A | 2/1999 | Kato | |
| 5,882,774 A | 3/1999 | Jonza | |
| 5,919,551 A | 7/1999 | Cobb, Jr. | |
| 5,925,715 A | 7/1999 | Mitra | |
| 5,962,550 A | 10/1999 | Akahane | |
| 5,965,632 A | 10/1999 | Orlowski | |
| 6,030,606 A | 2/2000 | Holmes | |
| 6,096,925 A | 8/2000 | Lee | |
| 6,111,696 A | 8/2000 | Allen | |
| 6,277,471 B1 | 8/2001 | Tang | |
| 6,280,063 B1 | 8/2001 | Fong | |
| 6,354,709 B1 | 3/2002 | Campbell | |
| 6,372,829 B1 | 4/2002 | Lamanna | |
| 6,387,981 B1 | 5/2002 | Zhang | |
| 6,428,862 B1 | 8/2002 | Noguchi | |
| 6,572,693 B1 | 6/2003 | Wu | |
| 6,577,358 B1 | 6/2003 | Arakawa | |
| 6,670,436 B2 | 12/2003 | Burgath | |
| 6,730,156 B1 | 5/2004 | Windisch | |
| 6,740,413 B2 | 5/2004 | Klun | |
| 6,750,352 B2* | 6/2004 | Ono et al. | 548/341.5 |
| 6,759,113 B1 | 7/2004 | Tang | |
| 6,765,038 B2 | 7/2004 | Mitra | |
| 7,074,463 B2 | 7/2006 | Jones | |
| 7,090,721 B2 | 8/2006 | Craig | |
| 7,090,722 B2 | 8/2006 | Budd | |
| 7,156,911 B2 | 1/2007 | Kangas | |
| 7,241,437 B2 | 7/2007 | Davidson | |
| 7,269,327 B2 | 9/2007 | Tang | |
| 7,269,328 B2 | 9/2007 | Tang | |
| 7,345,137 B2 | 3/2008 | Hebrink | |
| 7,452,924 B2 | 11/2008 | Aasen | |
| 7,553,881 B2 | 6/2009 | Salz | |
| 7,649,029 B2 | 1/2010 | Kolb | |
| 7,674,850 B2 | 3/2010 | Karim | |
| 2002/0057564 A1 | 5/2002 | Campbell | |
| 2002/0137825 A1 | 9/2002 | Lamanna | |
| 2003/0129421 A1 | 7/2003 | Terauchi | |
| 2004/0054041 A1 | 3/2004 | Schmidt | |
| 2004/0077775 A1 | 4/2004 | Audenaert | |
| 2006/0216500 A1 | 9/2006 | Klun | |
| 2007/0194275 A1 | 8/2007 | Masuda | |
| 2008/0027231 A1 | 1/2008 | Armstrong | |
| 2008/0051605 A1 | 2/2008 | Ricks-Laskoski | |
| 2008/0070966 A1 | 3/2008 | Elder | |
| 2008/0124555 A1 | 5/2008 | Klun | |
| 2008/0125559 A1 | 5/2008 | Radosz | |
| 2008/0134895 A1 | 6/2008 | Ruud | |
| 2008/0182917 A1 | 7/2008 | Miyabayashi | |
| 2008/0224089 A1 | 9/2008 | Pei | |
| 2009/0017256 A1 | 1/2009 | Hunt | |
| 2009/0060859 A1 | 3/2009 | Garcia Castro | |
| 2009/0142562 A1 | 6/2009 | Miyagawa | |
| 2009/0239969 A1 | 9/2009 | Orlowski | |
| 2010/0051509 A1* | 3/2010 | Martinez Palou et al. | 208/237 |
| 2011/0076424 A1 | 3/2011 | Pellerite | |
| 2011/0288227 A1 | 11/2011 | Lewandowski | |

FOREIGN PATENT DOCUMENTS

| | | |
|---|---|---|
| EP | 2067797 | 6/2009 |
| GB | 2449926 | 12/2008 |
| JP | 5-98049 | 4/1993 |
| JP | 5-163317 | 6/1993 |
| JP | 6-128501 | 5/1994 |
| JP | 61-36355 | 5/1994 |
| JP | 6-180859 | 6/1994 |
| JP | 07-041528 | 2/1995 |
| JP | 9-268260 | 10/1997 |
| JP | 2002-105058 | 4/2002 |
| JP | 2003-149875 | 5/2003 |
| JP | 2004-006232 | 1/2004 |
| JP | 2004-255481 | 9/2004 |
| JP | 2005-223967 | 8/2005 |
| JP | 2005-255843 | 9/2005 |
| JP | 2006/137885 | 6/2006 |
| JP | 2006-519164 | 8/2006 |
| JP | 2007/308616 | 11/2007 |
| JP | 2007-320093 | 12/2007 |
| JP | 2008-285670 | 11/2008 |
| JP | 2009/049397 | 3/2009 |
| JP | 2009-149828 | 7/2009 |
| JP | 2009-173925 | 8/2009 |
| JP | 2009-179671 | 8/2009 |
| JP | 2009-179727 | 8/2009 |
| JP | 2009173925 A * | 8/2009 |
| JP | 2009-209219 | 9/2009 |
| JP | 2009-227949 | 10/2009 |
| JP | 2009-263627 | 11/2009 |
| WO | WO 97/05182 | 2/1997 |
| WO | WO 01/30305 | 5/2001 |
| WO | WO 01/30306 | 5/2001 |
| WO | WO 01/30307 | 5/2001 |
| WO | WO 02/055011 | 7/2002 |
| WO | WO 03/063804 | 8/2003 |
| WO | WO 2004/069215 | 8/2004 |
| WO | WO 2006/026064 | 3/2006 |
| WO | WO 2006/053083 | 5/2006 |
| WO | WO 2006053083 A2 * | 5/2006 |
| WO | WO 2007/030679 | 3/2007 |
| WO | WO 2007/030715 | 3/2007 |
| WO | WO 2008/021533 | 2/2008 |
| WO | WO 2009/029438 | 3/2009 |
| WO | WO 2009/134694 | 11/2009 |
| WO | WO 2010/070819 | 6/2010 |
| WO | WO 2011/025847 | 3/2011 |
| WO | WO 2011/025963 | 3/2011 |
| WO | WO 2011/031442 | 3/2011 |
| WO | WO 2011/087621 | 7/2011 |
| WO | WO 2011/146356 | 11/2011 |

OTHER PUBLICATIONS

Akimoto et al., "Polymere Modellmembranen", Angew. Chemie., vol. 93, No. 1, 1981, pp. 108-109.

Anderson et al., "Solubility of $CO_2$, $CH_4$, $C_2H_6$, $C_2H_4$, $O_2$, and $N_2$ in 1-Hexyl-3methylpyridinium Bis(trifluoromethylsulfonyl)imide: Comparison to Other Ionic Liquids", Accounts of Chemical Research, 2007, 40, 1208-1216.

Antonucci et al., "Synthesis, Characterization and Evalutaion of Novel, Anti-Bacterial Monomers for Dental and Biomedical Applications", vol. 50, No. 2, Aug. 16, 2009, pp. 132-133, [[retrieved from the internet]] <http://www.nist.gov/manuscript-publication-search.cfm?pub_id=901947>.

Angell et al., "Parallel Developments in Aprotic and Protic Ionic Liquids: Physical Chemistry and Applications", Accounts of Chemical Research, 2007, 40, 1228-1236.

Baranyai et al., "Thermal Degradation of Ionic Liquids at Elevated Temperatures", Aust. J. Chem. 2004, 57, 145-147.

Bowyer et al., "Indium-Mediated Addition of 4-Bromocrotonic Acid to Aldehydes and Ketones—A Simple, High Yielding Route to α-Allyl-β-Hydroxy Carboxylic Acids", Aust. J. Chem. 2004, 57, 135-137.

Castner, Jr. et al., "Intermolecular Dynamics, Interactions, and Solvation in Ionic Liquids", Accounts of Chemical Research, 2007, 40, 1217-1227.

(56) References Cited

OTHER PUBLICATIONS

Diao et al., "High Performance Cross-Linked Poly(2-acrylamido-2-methylpropanesulfonic acid)-Based Proton Exchange Membranes for Fuel Cells", Macromolecules, vol. 43, Jul. 14, 2010, pp. 6398-6405.
Earle et al., "Keto-Enol Tautomerism as a Polarity Indicator in Ionic Liquids", Aust. J. Chem. 2004, 57, 149-150.
Fainerman-Melnikova et al., "Metal-Ion Recognition-Selective Bulk Membrane Transport of Silver(I) Using Thioether Donor Macrocycles as Ionophores, and X-Ray Structure of the Silver Complex of an $S_4$-Donor Ring", Aust. J. Chem. 2004, 57, 161-166.
Forsyth et al., "Ionic Liquids Based on Imidazolium and Pyrrolidinium Salts of the Tricyanomethanide Anion", Aust. J. Chem. 2004, 57, 121-124.
Forsyth et al., "Ionic Liquids—An Overview", Aust. J. Chem. 2004, 57, 113-119.
Friberg et al. "Copolymerization in a Non-Aqueous Lyotropic Liquid Crystal", Journal of Dispersion Science and Technology, vol. 14, No. 2, Jan. 1, 1993; 205-235.
Friberg et al., "Molecular Location in a Nonaqueous Lyotropic Liquid Crystal Polymer", Journal of Polymer Science, Part A, vol. 28, 1990, pp. 3575-3585.
Friberg, "Polyelectrolyte Synthesis in a Lamellar Liquid Crystal", Ber. Bundesges. Phys. Chem., vol. 100, No. 6, 1996, pp. 1083-1086.
Gou et al., "Measurement of the Dissolved Oxygen Concentration in Acryalte Monomers with a Novel Photochemical Methods", Journal of Polymer Science, Polym. Sci.: Part A: Polymer Chemistry. vol. 42, (2004), pp. 1285-1292.
Green et al., (2009) "The Design of Polymeric Ionic Liquids for the Preparation of Functional Materials", Polymer Reviews 49: 4, 339-360.
Guest Editorial, "Ionic Liquids", Accounts of Chemical Research, 2007, 40, 1077-1078.
Han et al., "Ionic Liquids in Separations", Accounts of Chemical Research, 2007, 40, 1079-1086.
Hardcare et al., "Structure and Solvation in Ionic Liquids", Accounts of Chemical Research, 2007, 40, 1146-1155.
Hemeon et al., Manganese Dioxide Allylic and Benzylic Oxidation Reactions in Ionic Liquids, Aust. J. Chem. 2004, 57, 125-128.
Hu et al., "Room-Temperature Ionic Liquids: Slow Dynamics, Viscosity, and the Red Edge Effect", Accounts of Chemical Research, 2007, 40, 1097-1105.
Ilesinghe et al., "An Evaluation of Some Hindered Diamines as Chiral Modifiers of Metal-Promoted Reactions", Aust. J. Chem. 2004, 57, 167-176.
Iwata et al., "Local Structure Formation in Alkyl-imidazolium-Based Ionic Liquids as Revealed by Linear and Nonlinear Raman Spectroscopy", Accounts of Chemical Research, 2007, 40, 1174-1181.
Jimenez et al., "Frontal Polymerization with Monofunctional and Difunctional Ionic Liquid Monomers", Journal of Polymer Science: Part A: Polymer Chemistry, vol. 45, 2745-2754 (2007).
Jimenez et al., "Photopolymerization Kinetics of Ionic Liquid Monomers Derived From the Neutralization Reaction Between Trialkylamines and Acid-Containing (Meth)Acrylates", Journal of Polymer Science: Part A: Polyer Chemistry, pp. 3009-3021 (Dec. 2006/Feb. 2007).
Juger et al., "Synthesis, Polymerization and Conducting Properties of an Ionic Liquid-Type Anionic Monomer", Tatrahedron Letters 50 (2009) 128-131.
Kapakoglou et al., "Coacervation of Surface-Functionalized Polymerized Vesicles Derived from Ammonium Bromide Surfactants. Application to the Selective Speciation of Chromium in Environmental Samples", Anal. Chem., vol. 80, 2008, pp. 9787-9796.
Klee et al., "Monomers for low shrinking composites, $2^a$—Synthesis of branched methacrylates and their application in dental composites," Macromolecular Chemistry and Physics, vol. 200, Issue 3, pp. 517-523, (1999).
Lu et al., "Advanced Applications of Ionic Liquids in Polymer Science", Progress in Polymer Science 34, (2009), 431-448.

Lynden-Bell et al., "Simulations of Ionic Liquids, Solutions, and Surfaces", Accounts of Chemical Research, 2007, 40, 1138-1145.
Macfarlane et al., "Ionic Liquids in Electrochemical Devices and Processes: Managing Interfacial Electrochemistry", Accounts of Chemical Research, 2007, 40, 1165-1173.
Maginn, "Atomistic Simulation of the Thermodynamic and Transport Properties of Ionic Liquids", Accounts of Chemical Research, 2007, 40, 1200-1207.
Mathis et al. "Properties of a New Glass Ionomer/Composite Resin Hybrid Restorative", Abstract No. 51, J. Dent. Res., 66:113 (1987).
Matijevic, Surface & Colloid Science, vol. 6 ed., Wiley Interscience (1973), pp. 23-29.
Meindersma et al., "Ionic Liquids", Ullmann's Encyclopedia of Industrial Chemistry, 2007.
Mosmuller et al., "Lipase Activity in Vesicular Systems: Characterization of *Candida cylindracea* Lipase and Its Activity in Polymerizable Dialkylammonium Surfactant Vesicles", Biotechnology and Boiengineering, vol. 42, 1993, 196-204.
Nakajima, "Preparation of Termally Stable Polymer Electrolytes From Imidazolium-Type Ionic Liquid Derivatives", Science Direct, Polymer 46 (2005) 11499-11504.
Ohno et al., "Amino Acid Ionic Liquids", Accounts of Chemical Research 2007, 40, 1122-1129.
Ohno et al., "Development of new class of ion conductive polymers based on ionic liquids", Electrochimica ACTA, vol. 50, No. 2-3, Nov. 30, 2004, pp. 254-260.
Ohno, "Design of Ion Conductive Polymers Based on Ionic Liquids", Macromol. Symp. 2007, pp. 551-556.
Olivier-Bourbigou et al.; "Ionic Liquids and Catalysis: Recent Progress From Knowledge to Applications", Applied Catalysis A: General 373 (2010) 1-56.
Padua et al., Molecular Solutes in Ionic Liquids: A Structural Perspective, Accounts of Chemical Research, 2007, 40, 1087-1096.
Plechkova et al., "Applications of ionic liquids in the chemical industry", Chemical Society Reviews, 2008, 37, pp. 123-150.
Popolo et al., "Clusters, Liquids and Crystals of Dialkyimidazolium Salts. A Combined Perspective from ab Initio and Classical Computer Simulations", Accounts of Chemical Research, 2007, 40, 1156-1164.
Rebelo et al., "Accounting for the Unique Double Dual Nature of Ionic Liquids from a Molecular Thermodynamic and Modeling Standpoint", Accounts of Chemical Research, 2007, 40, 1114-1121.
Ruckenstein et al., "Binding Catalytic Sites to the Surface of Porous Polymers and Some Catalytic Application", Chem. Mater. 1992, vol. 4, pp. 122-127.
Shim et al., "Solvation, Solute Rotation and Vibration Relaxation, and Electrom-Transfer Reactions in Room-Temperature Ionic Liquids", Accounts of Chemical Research 2007, 40, 1130-1137.
Smiglak et al., "The Second Evolution of Ionic Liquids: From Solvents and Separations to Advanced Materials—Energetic Examples From the Ionic Liquid Cookbook", Accounts of Chemical Research 2007, 40, 1182-1192.
Soulivong et al., "A Long-Chain Phosphine Designed as a Metal-lomesogen Generator—Synthesis and Coordination Properties", Aust. J. Chem. 2004, 57, 157-160.
Tan et al., "Photopolymerization and Characteristics of Reactive Organoclay-Polyurethane Nanocomposites", Polymer Composites, vol. 30, No. 5, Oct. 20, 2008, pp. 612-618.
Torimoto et al., "New Frontiers in Materials Science Opened by Ionic Liquids", Adv. Mater. 2009, 21, 1-26.
Tundo et al., Functionally Polymerized Surfactant Vesicles. Synthesis and Characterization, J. Am. Chem. Soc., vol. 104, 1982, pp. 456-461.
Vijayaraghavan et al., "Charge Transfer Polymerization in Ionic Liquids", Aust. J. Chem. 2004, 57, 129-133.
Wang et al., "Understanding Ionic Liquids through Atomistic and Coarse-Grained Molecular Dynamics Simulations", Accounts of Chemical Research, 2007, 40, 1193-1199.
Watts et al., "Determination of Polymerization Shrinkage Kinetics in Visible Light-Cured Materials: Methods Development", Dental Materials Oct. 1991, pp. 281-286.

(56) References Cited

OTHER PUBLICATIONS

Whitehead et al., "Analysis of Gold in Solutions Containing Ionic Liquids by Inductively Coupled Plasma Atomic Emission Spectrometry", Aust. J. Chem. 2004, 57, 151-155.

Yoshizawa et al., "Design of Ionic Liquids for Electrochemical Applications", Aust. J. Chem. 2004, 57, 139-144.

Yoshizawa et al., "Novel Polymer Electrolytes Prepared by Copolymerization of Ionic Liquid Monomers", Polymers for Advanced Technologies 13, 589-594 (2002).

Zaderenko, et al., "Synthesis and Regioselective Hydrolysis of 2-Imidazol-1-ylsuccinic Esters," Journal of Organic Chemistry, vol. 59, Issue 21, pp. 6268-6273, (1994).

The Dental Advisor; 3M ESPE Filtek™ Z250 Universal Restorative 9-year Clinical Performance+++++; Jun. 2008, 2 pages.

Partial International Search Report PCT/US2010/059033, May 8, 2012, 3 pages.

International Search Report PCT/US2010/059033 Jun. 28, 2012, 6 pages.

* cited by examiner

US 8,853,338 B2

CURABLE DENTAL COMPOSITIONS AND ARTICLES COMPRISING POLYMERIZABLE IONIC LIQUIDS

CROSS REFERENCE TO RELATED APPLICATIONS

This application is a national stage filing under 35 U.S.C. 371 of PCT/US2010/059033, filed Dec. 6, 2010, which claims priority to U.S. Provisional Application No. 61/289,098, filed Dec. 22, 2009 and 61/360,159, filed Jun. 30, 2010, the disclosure of which is incorporated by reference in their entirety herein.

BACKGROUND

Ionic liquids (ILs) are salts in which the cation and anion are poorly coordinated. At least one of the ionic components is organic and one of the ions has a delocalized charge. This prevents the formation of a stable crystal lattice, and results in such materials existing as liquids, often at room temperature, and at least, by definition, at less than 100° C. For example, sodium chloride, a typical ionic salt, has a melting point of about 800° C., whereas the ionic liquid N-methylimidazolium chloride has a melting point of about 75° C.

Ionic liquids typically comprise an organic cation, such as a substituted ammonium or a nitrogen-containing heterocycle, such as a substituted imidazolium, coupled with an inorganic anion. However, species have also been described wherein the cation and anion are organic. When the ionic liquid comprises at least one polymerizable group, such ionic liquid is a polymerizable ionic liquid ("PIL").

SUMMARY

Presently described are curable dental compositions comprising a polymerizable ionic liquid. The polymerizable ionic liquid comprises one or more ethylenically unsaturated (e.g. free-radically polymerizable) groups. Various embodiments of curable dental compositions are described. In some embodiments, the polymerizable ionic liquid is a monofunctional polymerizable ionic liquid comprising an ethylenically unsaturated group. In other embodiments, the polymerizable ionic liquid is a multifunctional polymerizable ionic liquid comprising at least two ethylenically unsaturated groups. The curable dental compositions describe herein can be utilized as dental primers, dental adhesives, dental sealants, and dental composites. In many embodiments, the curable dental compositions further comprise an initiator such as a photoinitiator.

Also described are various dental articles, comprising the cured composition as described herein. Such dental articles can be highly filled dental compositions such as a filling, crown, bridge, or restoration for an implant.

Also described are dental articles, such as a filling, crown, bridge, or a restoration for an implant, comprising the cured adhesive or cured coating as described herein.

Also described are methods of making a dental restoration and method of use of dental compositions that comprise curing the dental compositions. The compositions can advantageously be cured in air.

DETAILED DESCRIPTION

As used herein, "dental composition" refers to an unfilled material (i.e. total dental composition except for filler) or filled material (e.g., a dental cement or restoration) capable of adhering or being bonded to an oral surface. A curable dental composition can be used to bond a dental article to a tooth structure, form a coating (e.g. sealant) on a tooth surface, or can be used to fabricate a preformed (e.g. crown or bridge) restorative Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., orthodontic sealants), and varnishes; and composites (also referred to as restorations) such as dental fillings, as well as crowns and bridges. Highly filled dental compositions are also used for mill blanks, from which a crown may be milled. A composite is a highly filled paste designed to be suitable for filling substantial voids in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding a dental restorations such as a crown, bridge, or implant. As used herein, "dental article" refers to an article that can be adhered (e.g., bonded) to a tooth structure. Dental articles include, for example, crowns, bridges, veneers, inlays, onlays, fillings, orthodontic appliances and devices.

As used herein, "orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

As used herein, an "oral surface" refers to a soft or hard surface in the oral environment. Hard surfaces typically include tooth structure including, for example, natural and artificial tooth surfaces, bone, and the like.

As used herein, "hardenable" is descriptive of a material or composition that can be cured (e.g., polymerized or crosslinked) by heating to induce polymerization and/or crosslinking; irradiating with actinic irradiation to induce polymerization and/or crosslinking; and/or by mixing one or more components to induce polymerization and/or crosslinking "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked).

As used herein, "hardener" refers to something that initiates hardening of a resin. A hardener may include, for example, a polymerization initiator system, a photoinitiator system, a thermal initiator and/or a redox initiator system.

As used herein, the term "(meth)acrylate" is a shorthand reference to acrylate, methacrylate, or combinations thereof "(meth)acrylic" is a shorthand reference to acrylic, methacrylic, or combinations thereof and "(meth)acryl" is a shorthand reference to acryl, methacryl, or combinations thereof. As used herein, "a," "an," "the," "at least one," and "one or more" are used interchangeably.

Unless specified otherwise, "alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

Unless specified otherwise, "heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent.

Unless specified otherwise, "aromatic group" or "aromatic moiety" includes 6-18 ring atoms and can contain optional fused rings, which may be saturated or unsaturated. Examples of aromatic groups include phenyl, naphthyl, biphenyl, phenanthryl, and anthracyl. The aromatic group may optionally contain 1-3 heteroatoms such as nitrogen, oxygen, or sulfur and can contain fused rings. Examples of aromatic group having heteroatoms include pyridyl, furanyl, pyrrolyl, thienyl, thiazolyl, oxazolyl, imidazolyl, indolyl, benzofuranyl, and benzthiazolyl. Unless otherwise noted the aromatic group may be mono- or polyvalent.

Also herein, the recitations of numerical ranges by endpoints include all numbers subsumed within that range (e.g., 1 to 5 includes 1, 1.5, 2, 2.75, 3, 3.80, 4, 5, etc.).

Presently described are various curable dental compositions that comprise a polymerizable ionic liquid, comprising a cation and anion that are poorly coordinated. Such polymerizable ionic liquids have a melting point ($T_m$) below about 100° C. The melting point of these compounds is more preferably below about 60° C., 50° C., 40° C., or 30° C. and most preferably below about 25° C., for ease of use in various polymerizable dental compositions as described herein with or without the aid of solvent carriers in the composition. Polymerizable ionic liquids having a melting point below 25° C. are liquids at ambient temperature. As the molecular weight of the polymerizable ionic liquid increases, the viscosity can increase. In some embodiments, the molecular weight is less than 1000 g/mole.

Suitable cationic groups, also known as onium salts, include substituted ammonium salts, substituted phosphonium salts, substituted pyridinium salts, and substituted imidazolium salts. The structures of the cations of such onium salts are depicted as follows:

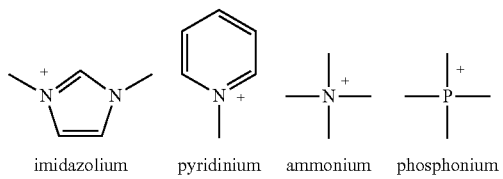

imidazolium    pyridinium    ammonium    phosphonium

Other cationic groups include pyrazolium, pyrrolidinium, and cholinium.

The anion may be organic or inorganic, and is typically a monovalent anion, i.e. having a charge of −1. Illustrative examples of anions useful herein include various organic anions such as carboxylates ($CH_3CO_2^-$, $C_2H_5CO_2^-$, $ArCO_2^-$), sulfates ($HSO_4^-$, $CH_3SO_4^-$), sulfonates ($CH_3SO_3^-$), tosylates, and fluoroorganics ($CF_3SO_4^-$, $(CF_3SO_2)_2N^-$, $(C_2F_5SO_2)_2N^-$, $(C_2F_5SO_2)(CF_3SO_2)N^-$, $CF_3CO_2^-$, $CF_3C_6F_4SO_3^-$, $CH_3C_6F_4SO_3^-$, tetrakis(pentafluorophenyl)borate).

In some embodiments, curable dental compositions are described comprising a polymerizable ionic liquid comprising an aromatic carboxylate anion $ArCO_2^-$. Such polymerizable ionic liquids may comprise a (e.g. free-radically) polymerizable anion, a (e.g. free-radically) polymerizable cation, or both a (e.g. free-radically) polymerizable anion and a (e.g. free-radically) polymerizable cation. In some embodiments, the cation is a substituted ammonium, phosphonium, or imidazolium cation.

The anion may alternatively be an inorganic anion such as $ClO_4^-$, fluoroinorganics ($PF_6^-$, $BF_4^-$, $AsF_6^-$, $SbF_6^-$) and halides ($Br^-$, $I^-$, $Cl^-$). In some embodiments, the anion is preferably an organic anion such as a sulfonate. Organic anions may be non-halogenated which is amenable to providing dental compositions that are halogen-free. In some embodiments, the (e.g. sulfonate) anion is non-fluorinated and lacks an aromatic substituent. Further, in some embodiments, the anion lacks ethylenically unsaturated groups and is a non-polymerizable anion. In other embodiments, the organic anion is polymerizable.

The polymerizable groups are ethylenically unsaturated terminal polymerizable groups. The ethylenically unsaturated groups are preferably free-radically polymerizable groups including (meth)acryl such as (meth)acrylamide ($H_2C$=$CHCON$— and $H_2C$=$CH(CH_3)CON$—) and (meth)acrylate($CH_2CHCOO$— and $CH_2C(CH_3)COO$—). Other ethylenically unsaturated (e.g. free-radically) polymerizable groups include vinyl ($H_2C$=$C$—) including vinyl ethers ($H_2C$=$CHOCH$—). The methacrylate functional onium salts are typically preferred over the acrylate onium salts in curable dental compositions because they exhibit a slower rate of cure.

The polymerizable ionic liquid functions as a reactive monomer and thus is substantially unpolymerized in the curable dental composition at the time the curable dental composition is applied to a tooth surface or formed into a dental article such as a crown. Hence, the curable composition hardens upon curing via polymerization of the ethylenically unsaturated groups of the (e.g. multifunctional) polymerizable ionic liquid. Such curing generally results in a permanent bond. For example, when the curable dental composition is an adhesive, the bonded dental article (e.g. crown restoration) typically cannot be separated without damaging such article.

In some embodiments, the polymerizable ionic liquid is monofunctional, having one polymerizable ethylenically unsaturated group. Monofunctional polymerizable ionic liquids have been found to be particularly suitable for dental primers. In this embodiment, the ethylenically unsaturated group of the monofunctional polymerizable ionic liquid is typically cured concurrently with the curable (e.g. adhesive) composition that is applied to the primer. Monofunctional polymerizable ionic liquids can also be combined with conventional multifunctional ethylenically unsaturated (e.g. (meth)acrylate) monomers to enhance curing thereby minimizing the formation of a surface residue surmised to be caused by oxygen curing inhibition of curable dental compositions.

In other embodiments, the polymerizable ionic liquid is multifunctional, typically comprising two or three polymerizable groups. For example, in some embodiments the polymerizable ionic liquid may comprise a polymerizable cation and a polymerizable anion. In other embodiments, the multifunctional polymerizable ionic liquids described herein can be characterized as having a multifunctional cation, having two, three, or more polymerizable groups bonded to the same cationic group.

In some embodiments, the polymerizable ionic liquid is a mixture comprising at least one multifunctional polymerizable ionic liquid and at least one monofunctional polymerizable ionic liquid.

In some favored embodiments, the curable dental composition comprises a new class or new species of polymerizable ionic liquids. In some favored embodiments the curable dental compositions comprise a multifunctional cation, having two or more polymerizable groups, each bonded to the same cationic group via a divalent non-alkylene linking group. Such multifunctional polymerizable ionic liquid is further described in U.S. Provisional Application Ser. No. 61/289,072 entitled "POLYMERIZABLE IONIC LIQUID COMPRISING MULTIFUNCTIONAL CATION AND ANTISTATIC COATINGS"; incorporated herein by reference. As used herein, linking groups refer to the entirety of the chain of atoms between the (e.g. single) cation and ethylenically unsaturated terminal group. Although the linking groups may and often comprises lower alkyl segments, e.g. of 1 to 4 carbon atoms, the linking groups further comprise other atoms within the carbon backbone and/or other groups pendant to the (e.g. carbon) backbone. Most commonly, the linking groups comprise heteroatoms such as sulfur, oxygen, or nitrogen, and more commonly oxygen or nitrogen. The linking groups may comprise linkages such as amide (—CONR—) or ether (—COC—) linkages and more commonly urethane (—ROCONR—), urea (—RNCONR—), or ester linkages (—COOR—); wherein R is a lower alkyl of 1-4 carbon atoms.

For embodiments wherein the cation is ammonium or phosphonium, the polymerizable ionic liquid may have the general formula:

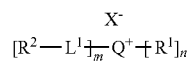

wherein:
Q is nitrogen or phosphorous;
$R^1$ is independently hydrogen, alkyl, aryl, alkaryl, or a combination thereof;
$R^2$ is independently an ethylenically unsaturated group;
$L^1$ is independently a linking group with the proviso that at least two of the linking groups are not alkylene linking groups;
m is an integer of 2 to 4;
n is an integer of 0 to 2;
and m+n=4; and
X is an anion.

At least two of the linking groups, $L^1$, are preferably linking groups that comprise one or more heteroatoms such as nitrogen, oxygen, or sulfur. In favored embodiments, at least two of the linking groups, $L^1$ comprise nitrogen or oxygen heteroatoms, such as linking groups that comprise an amide, urea, ether, urethane or ester linkage. The linking group may comprise more than one of such linkages.

Although each terminal ethylenically unsaturated group, $R^2$, bonded to each linking group can comprise a different ethylenically unsaturated group, the terminal ethylenically unsaturated group, $R^2$, is typically the same ethylenically unsaturated polymerizable group, such as the same vinyl, (meth)acrylamide, or (meth)acrylate group. In some embodiments, m is 3 and thus, the polymerizable ionic liquid is a trifunctional (e.g. tri(meth)acrylate) polymerizable ionic liquid. In other embodiments, m is 2 and thus, the polymerizable ionic liquid is a difunctional (e.g. di(meth)acrylate) polymerizable ionic liquid.

In some embodiments, n is at least 1. $R^1$ is typically hydrogen or a straight-chain lower alkyl of 1 to 4 carbon atoms. However, $R^1$ may optionally be branched or comprise a cyclic structure. $R^1$ may optionally comprise phosphorous, halogen, one or more heteroatoms such as nitrogen, oxygen, or sulfur.

Preferred polymerizable ionic species wherein the cation is ammonium include:

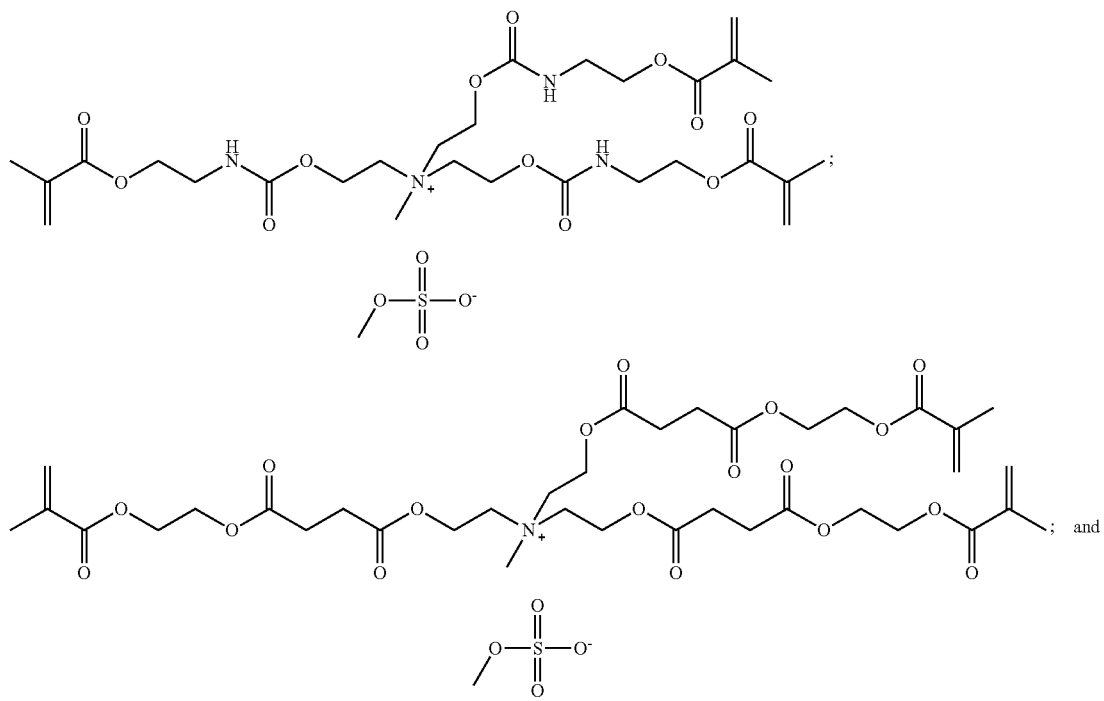

-continued

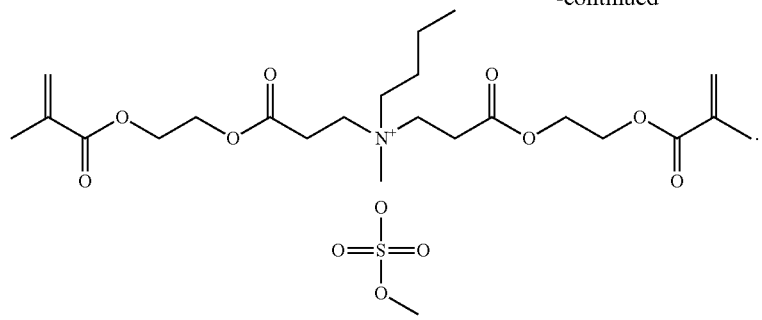

These species just described can include various other anions, as previously described.

In another favored embodiment, the curable dental composition comprises a monofunctional polymerizable ionic liquid comprising a non-polymerizable cation, such as a substituted imidazolium cation and a polymerizable anion. The imidazolium cation is typically substituted with one or two lower alkyl groups of 1 to 4 carbon atoms. The anion is preferably a (e.g. nonfluorinated) sulfonate anion. One favored species is

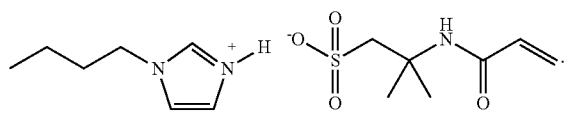

In other embodiments, a polymerizable ionic liquid and dental composition is described comprising a polymerizable cation and a polymerizable anion. In one embodiment, the polymerizable cation comprises an aromatic moiety. The polymerizable anion is preferably a carboxylate anion. Such class of polymerizable ionic liquids may be employed (in place of HEMA) in a resin modified glass ionomer restorative composition.

The polymerizable ionic liquid may comprise a substituted pyridinium cation. The polymerizable ionic liquid may have the general formula:

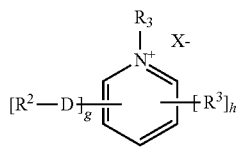

wherein $R^3$ is independently hydrogen or a C2-C8 alkyl group;

$R^2$ is an ethylenically unsaturated group;

D is a divalent linking group;

g is 1-5;

h is 0-4;

g+h=5; and $X^-$ is an organic cation comprising at least one ethylenically unsaturated group.

An illustrative species includes

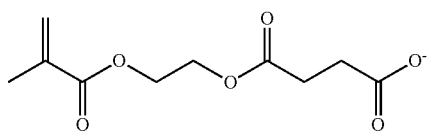

-continued

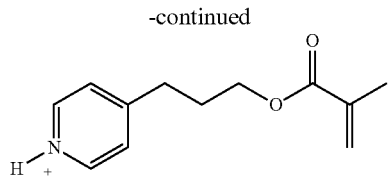

Alternatively, the polymerizable ionic liquid may comprise a substituted ammonium cation. The polymerizable ionic liquid may have the general formula:

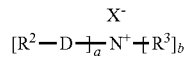

wherein $R^3$ is independently hydrogen or a C2-C8 alkyl group;

$R^2$ is an ethylenically unsaturated group;

D is a divalent linking group comprising an aromatic moiety;

a is 1-4;

b is 0-3;

a+b=4; and $X^-$ is an organic cation comprising at least one ethylenically unsaturated group. The ethylenically unsaturated group may be a vinyl group.

Some illustrative species include

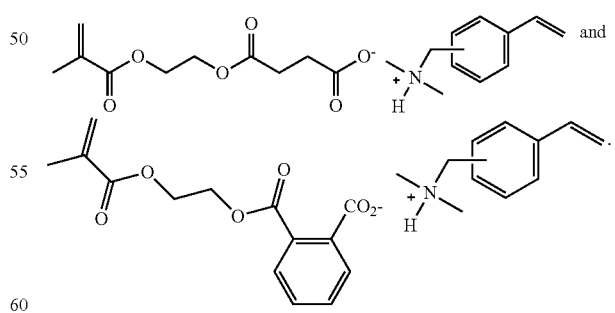

In another favored embodiment, the polymerizable composition comprises a polymerizable ionic liquid comprising an aromatic carboxylate anion.

Such (e.g. free-radically) polymerizable ionic liquids may have the general formula:

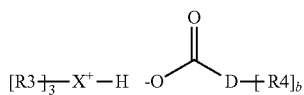

wherein
X is nitrogen or phosphorus;
R3 and R4 are independently alkyl or heteroalkyl, and at least one R3 or R4 comprises a free-radically polymerizable group;
D comprises an aromatic moiety and optionally comprises a linking group between the carboxylate end group and aromatic moiety and/or optionally comprises a linking group between the aromatic moiety and R4; and
b is 0-2.

The free-radically polymerizable groups are preferably (meth)acrylate groups. The aromatic moiety of D typically comprises one, two, or three aromatic rings that are optionally fused, such as in the case of phthalate or aromatic rings derived from biphenyl or triphenyl compounds.

In some embodiments, both the substituted (e.g. ammonium) cation and the aromatic carboxylate anion each comprise at least one free radically polymerizable group, such as (meth)acrylate groups. In some embodiments, two R3 are alkyl groups and one R3 group comprises a (meth)acrylate group. In another embodiment, two R3 are alkyl groups and one R3 group comprises an aromatic (e.g. phenyl) (meth)acrylate group. The alkyl groups of R3 typically comprise at least one carbon atom (e.g. methyl) and no greater than 8, or no greater than 6, or no greater than 4 carbon atoms. A linking group is typically present between the terminal (e.g. free-radically) polymerizable (meth)acrylate group and the (e.g. ammonium) cation (X$^+$), a previously described. D may comprise a divalent (e.g. ester) linking group between a (e.g. phenyl) aromatic group and terminal (meth)acrylate group.

Examples of such free-radically polymerizable ionic liquids include:

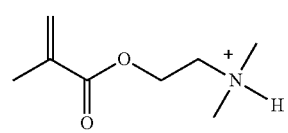

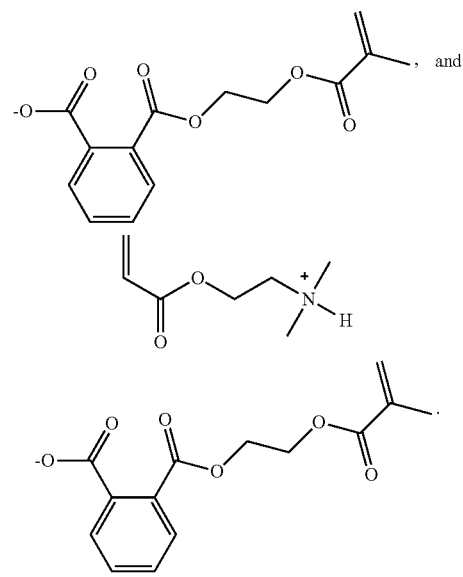

The species described herein can include various other anions, as previously described.

The polymerizable ionic liquids described herein can be made by several methods. One method includes reaction of a hydroxyl functional ionic precursor with a polymerizable isocyanate such as depicted by the following reaction scheme:

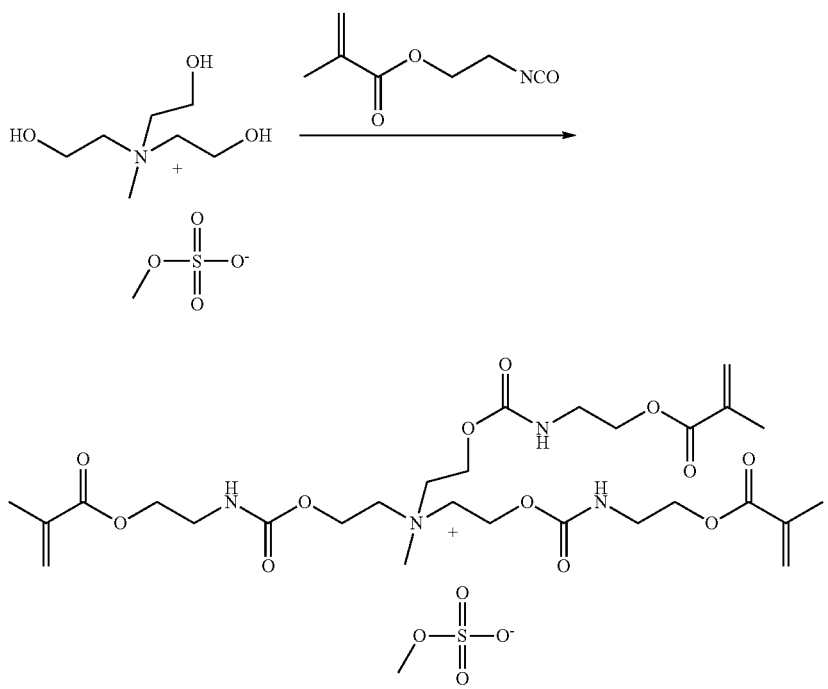

Commercially available starting materials include tris-(2-hydroxyethyl)-methyl ammonium methyl sulfate available from BASF (BASIONIC FS01), diethanolamine hydrochloride, 2-amino-1,3-propanediol hydrochloride, and tris(hydroxymethyl)aminomethane hydrochloride. The ionic product may be further reacted to exchange the anion using anion metathesis as described in "Ionic Liquids", Meindersma, G. W., Maase, M., and De Haan, A. B., Ullmann's Encyclopedia of Industrial Chemistry, 2007.

Another method includes the reaction of a hydroxyl functional amine precursor with a polymerizable isocyanate, followed by alkylation or acidification, such as depicted by the following reaction scheme:

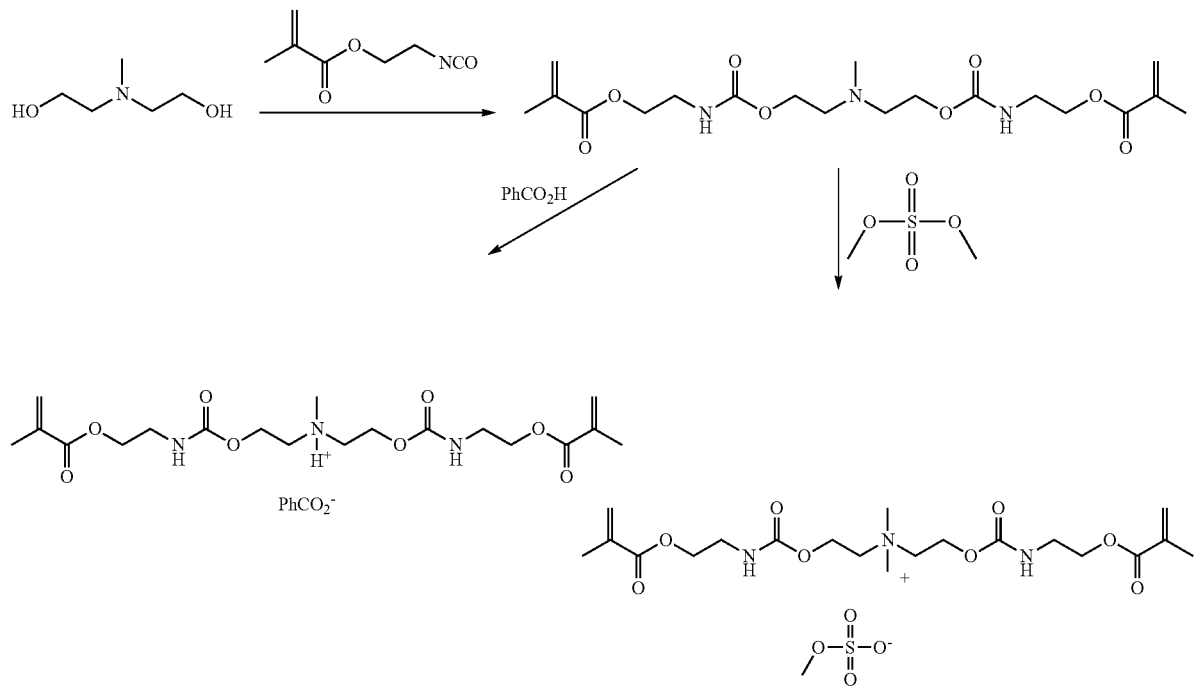

Commercially available starting materials include diethanol amine, diisopropanol amine, N-methyldiethanol amine, N-ethyldiethanol amine, N-butyldiethanol amine, triethanol amine, 1-[N,N-bis(2-hydroxyethyl)-amino]-2-propanol, triisopropanol amine, 3-amino-1,2-propanediol, 3-(dimethylamino)-1,2-propanediol, 3-(diethylamino)-1,2-propanediol, 3-(dipropylamino)-1,2-propanediol, 3-(diisopropylamino)1,2,-propanediol, 2-amino-1,3-propanediol, 2-amino-2-ethyl-1,3,-propanediol, 2-amino-2-methyl-1,3,-propanediol, tris(hydroxymethyl)amino methane, bis(2-hydroxyethyl)amino-tris(hydroxymethyl)methane, 2,2-bis(hydroxymethyl)-2,2',2"-nitrilotriethanol, N,N' bis(2-hydroxyethyl)-ethylenediamine, N-N-N'-N'-tetrakis(2-hydroxypropyl)-ethylenediamine, 1,3-bis[tris(hydroxymethyl)-methylamino]propane, 3-pyrrolidino-1,2-propanediol, 3-piperidino-1,2-propanediol, and 1,4-bis(2-hydroxyethyl)-piperazine.

Useful alkylating agents include alkyl halides, sulfates, and phosphonate esters, such as methyl iodide, ethyl iodide, methyl bromide, ethyl bromide, dimethyl sulfate, diethyl sulfate, and dimethyl methylphosphonate. Useful acidification agents include carboxylic acids, organosulfonic acids, and organophosphonic acids and inorganic acids such as hydrochloric acid, hydrofluoric acid, hydrobromic acid, phosphoric acid, nitric acid and the like.

Another method includes the reaction of an amine with an acrylate compound to give a polymerizable amine precursor, followed by alkylation or acidification, such as depicted by the following reaction scheme:

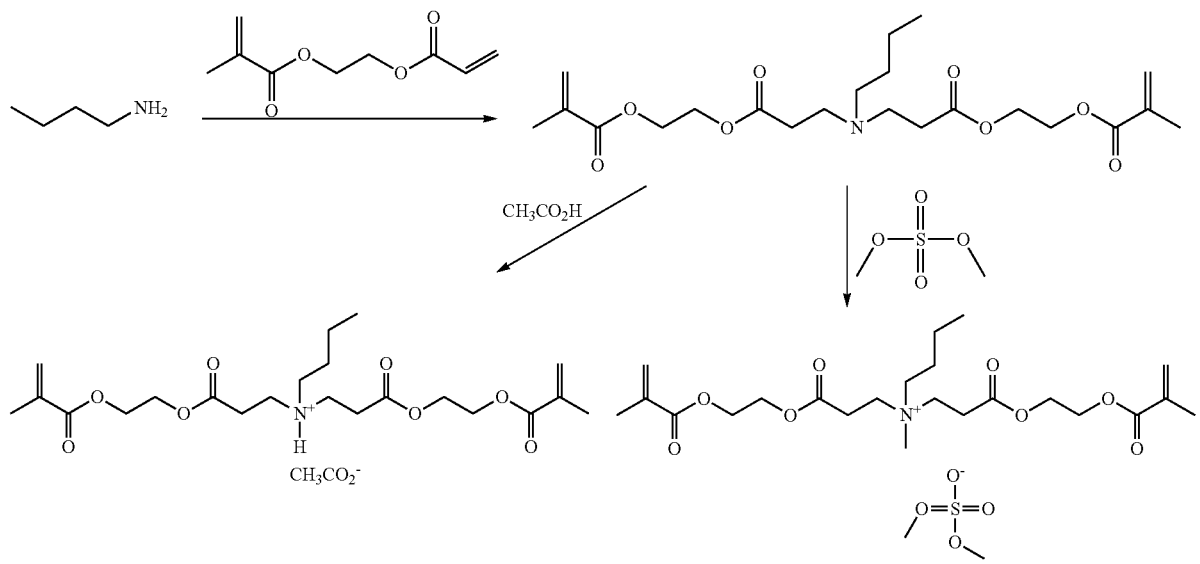

Commercially available starting materials include amines such as methylamine, ethylamine, propylamine, butylamine, hexylamine, isopropylamine, isobutylamine, 1-methylbutylamine, 1-ethyl propylamine, 2-methylbutylamine, isoamylamine, 1,2-dimethylpropylamine, 1,3-dimethylbutylamine, 3,3-dimethylbutylamine, 2-aminoheptane, 3-aminoheptane, 1-methylheptyamine, 2-ethylhexylamine, 1,5-dimethylhexylamine, cyclopropylamine, cyclohexylamine, cyclobutylamine, cyclopentylamine, cycloheptylamine, cyclooctylamine, 2-aminonorbornane, 1-adamantanamine, allylamine, tetrahydrofurfurylamine, ethanolamine, 3-amino-1-propanol, 2-(2-aminoethoxy)ethanol, benzylamine, phenethylamine, 3-phenyl-1-propylamine, 1-aminoindan, ethylenediamine, diaminopropane, and hexamethylenediamine.

Another method, that provides a polymerizable ionic liquid containing an ether linking group, includes the reaction of a hydroxyl functional precursor with a functionalized (meth)acrylate molecule such as depicted by the following reaction scheme:

Another method, that provides a polymerizable ionic liquid containing an amide linking group, includes the reaction of an amine functional precursor with a functionalized (meth)acrylate molecule such as depicted by the following reaction scheme:

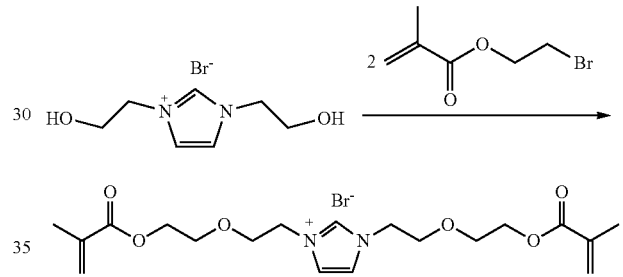

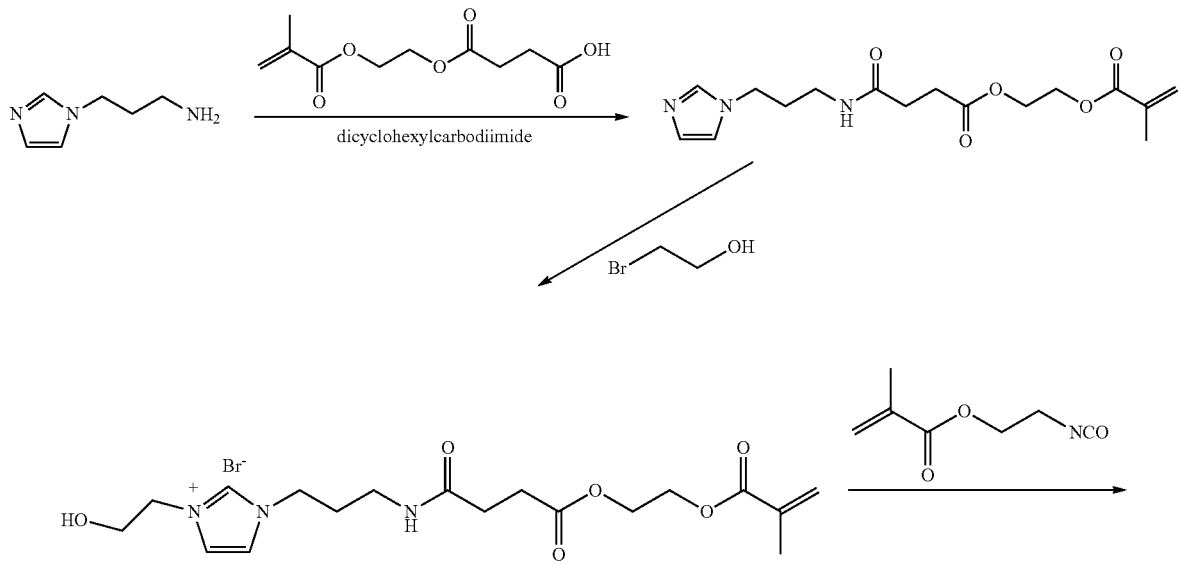

-continued

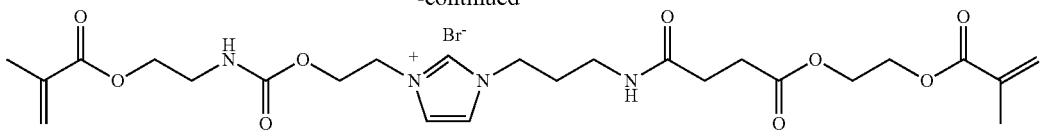

Another illustrative method, that provides a polymerizable ionic liquid containing a urea linking group, is depicted by the following reaction scheme:

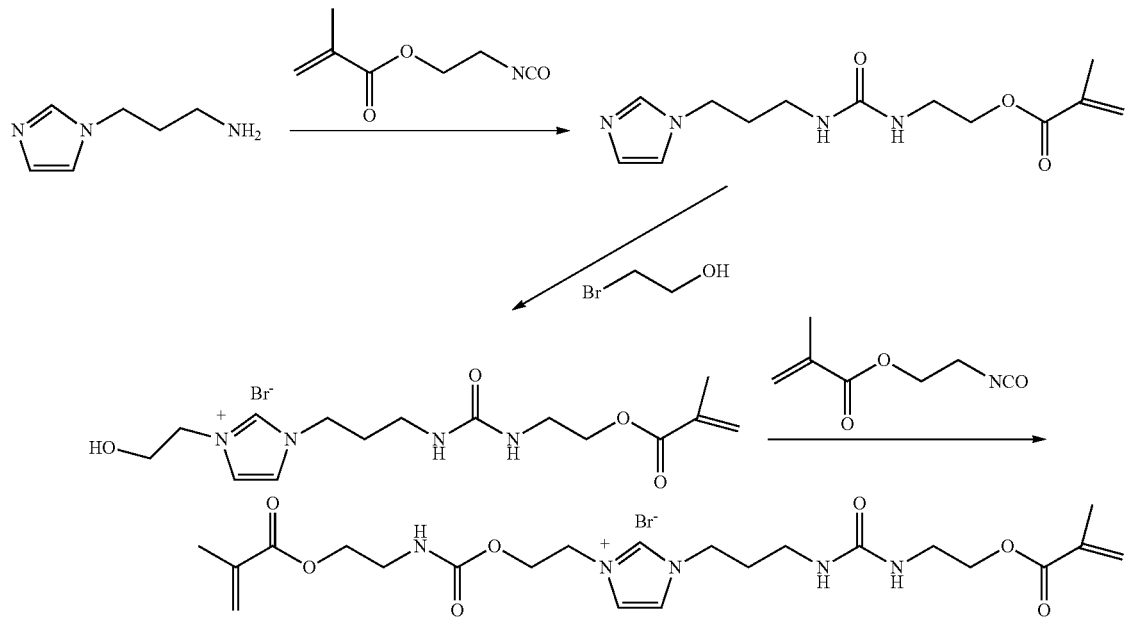

The polymerizable ionic liquid(s) may be present in the curable dental composition at a weight percentage of 1 to 99.95%.

In some embodiments, the polymerizable ionic liquid, such as a multifunctional polymerizable ionic liquid(s) is employed as the primary or sole polymerizable organic component, typically in combination with a polymerization initiator, such as a photoinitiator. Hence in this embodiment, the concentration of polymerizable ionic liquid in the (unfilled) curable dental composition is typically about 95 wt-%, 96 wt-%, 97 wt-%, or about 98 wt-%.

In preferred embodiments, the polymerizable ionic liquids are typically employed in combination with other conventional (e.g. (meth)acrylate) ethylenically unsaturated monomer(s), oligomer(s), or polymer(s). By "other" is it meant an ethylenically unsaturated monomer that is not a polymerizable ionic liquid. Although conventional monomers are polymerizable and many are liquids at 25° C., conventional monomers are typically non-ionic, lacking a cation and an anion.

It has been found that a polymerizable ionic liquid can be used in place of conventional hardenable (meth)acrylate monomers, such as 2-hydroxylethyl methacrylate (HEMA), triethyleneglycol dimethacrylate (TEGDMA), and 2,2-bis[4-(2-hydroxy-3-methacyloxypropoxy)phenyl]propane (Bis-GMA) that are commonly used in curable dental compositions. Such embodiment is amenable to providing a dental composition that is free of monomer derived from bisphenol A (such as BisGMA).

Preferred (e.g. multifunctional) polymerizable ionic liquids exhibit a high air to nitrogen curing exotherm ratio, as can be measured by photo DSC according to the test method described in the examples. The air to nitrogen curing ratio is typically at least 0.70 or 0.75. In preferred embodiments, the air to nitrogen curing exotherm ratio is typically at least the 0.80, 0.85, 0.90, or 0.95. For embodiments wherein the air to nitrogen curing ratio of the polymerizable ionic liquid is sufficiently high, the polymerizable ionic liquid can advantageously be substantially completely cured in air (i.e. an oxygen rich environment) rather than requiring curing in the absence of oxygen.

A substantially completely cured (i.e. hardened) polymerizable ionic liquid is solid at 25° C. and is substantially free of uncured polymerizable ionic liquid. When uncured polymerizable ionic liquid is present it typically results as a surface residue exhibiting a "wet" appearance. Minimal surface inhibition not only provides more complete curing but also minimizes the formation of a less cured oxygen inhibited surface. This provide the benefit of reduced extractables and also less need to remove the uncured "wet" monomer layer by use of an absorbant wiping material with or without a solvent such as ethanol The extent of curing can be determined by various methods known in art. One common method is to determine the amount of uncured material by solvent extraction. In preferred embodiments, the amount of uncured extractable polymerizable ionic liquid is less than 10%, more preferably less than 5%, and most preferably less than 1% by weight of the cured composition.

Conventional (meth)acrylate monomers typically have an air to nitrogen curing exotherm ratio of no greater than 0.50, 0.40, 0.35, 0.20, or 0.25 or lower. For example, TEGMA has been found to have an air to nitrogen curing exotherm ratio of about 0.36; whereas HEMA has been found to have an air to nitrogen curing exotherm ratio of less than 0.25. Although the photocuring of conventional (meth)acrylate monomers and especially methacrylate monomers is typically inhibited by oxygen present in air, the inclusion of the (e.g. multifunctional) polymerizable ionic liquid can sufficiently increase the air to nitrogen curing exotherm of the mixture such that the mixture can advantageously be substantially completely cured in air. For embodiments wherein the dental composition is to be cured in air and the (e.g. multifunctional) polymerizable ionic liquid is combined with another polymerizable (meth)acrylate component that exhibits a lower air to nitrogen curing exotherm ratio, the air to oxygen curing exotherm ratio of the (e.g. multifunctional) polymerizable ionic liquid, described herein, is preferably at least 0.85, 0.90, or 0.95.

The total concentration of (e.g. multifunctional) polymerizable ionic liquid(s) having a high air to nitrogen curing exotherm ratio, is typically at least 25 wt-%, 30 wt-%, 35 wt-%, and preferably at least 40 wt-% of the unfilled curable dental composition (the total polymerizable organic dental composition excluding inorganic filler). In this embodiment, the total concentration of other ethylenically unsaturated (e.g. (meth)acrylate) monomer(s), oligomer(s), and polymer(s) is typically at least 10 wt-%, 20 wt-%, 30 wt-%, 40 wt-%, 50 wt-%, 60 wt-% or 65 wt-%.

Although the presence of the (e.g. multifunctional) polymerizable ionic liquid having a high air to oxygen curing ratio is beneficial to curing, as just described, the presence of the other conventional (meth)acrylate monomer may also benefit the (e.g. multifunctional) polymerizable ionic liquid by improving the stability by hindering unintended polymerization, such as during storage, prior to (e.g. photo) curing. Thus, in at least some favored embodiments the amount of other ethylenically unsaturated (e.g. (meth)acrylate) monomer(s), oligomer(s) is typically at least 21 wt-%, 22 wt-%, 23 wt-%, 24 wt-%, or 25 wt-% of the unfilled curable dental composition. The concentration of (e.g. multifunctional)polymerizable ionic liquid(s) having a high air to oxygen curing ratio is less than 80 wt-%. Typically, it is preferred to maximize the concentration of other ethylenically unsaturated (e.g. (meth) acrylate) monomer(s), oligomer(s) provided that the air to oxygen curing ratio of the mixture is at least 0.75 and preferably at least 0.80, 0.85, 0.90 or greater. Depending on the selection of other ethylenically unsaturated (e.g. (meth)acrylate) monomer(s), oligomer(s), this concurrently can be achieved when the concentration of (e.g. multifunctional) polymerizable ionic liquid(s) having a high air to oxygen curing ratio is at least about 35 wt-%, 40 wt-%, or 45 wt-%.). For embodiments, wherein the other ethylenically unsaturated monomer(s), oligomer(s), and polymer(s) has an air to oxygen curing exotherm of about 0.25 or lower, the concentration of polymerizable ionic liquid may be at least 50 wt-%, 55 wt-%, or 60 wt-%.

In other embodiments, a small concentration of a polymerizable ionic liquid can be added to a conventional curable dental composition as an additive. The inclusion of such can improve adhesion to polar surfaces such as oral surfaces. In this embodiment, the amount of polymerizable ionic liquid is typically at least 0.5 wt-%, 1.0 wt-%, 2.0 wt-%, 3.0 wt-%, 4.0 wt-%, or 5.0 wt-% and generally no greater than about 30 wt-%, 20 wt-% or 10 wt-%.

In addition to the (e.g. multifunctional) polymerizable ionic liquids described herein, the curable component of the curable dental composition can include a wide variety of other ethylenically unsaturated compounds (with or without acid functionality), epoxy-functional (meth)acrylate resins, vinyl ethers, glass ionomer cements, and the like.

The (e.g., photopolymerizable) dental compositions may include compounds having free radically reactive functional groups that may include monomers, oligomers, and polymers having one or more ethylenically unsaturated group. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof. Such free radically polymerizable compounds include mono-, di- or poly-(meth)acrylates (i.e., acrylates and methacrylates) such as, methyl(meth)acrylate, ethyl(meth)acrylate, isopropyl (meth) acrylate, n-hexyl(meth)acrylate, stearyl(meth)acrylate, allyl (meth)acrylate, glycerol tri(meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain hydroxyl groups and ethylenically unsaturated groups in a single molecule. Examples of such materials include hydroxyalkyl (meth)acrylates, such as 2-hydroxyethyl(meth)acrylate and 2-hydroxypropyl(meth)acrylate; glycerol mono- or di-(meth) acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis [4-(2-hydroxy-3-ethacryloxypropoxy)phenyl]propane (bis-GMA). Suitable ethylenically unsaturated compounds are also available from a wide variety of commercial sources, such as Sigma-Aldrich, St. Louis.

In certain embodiments curable composition can include bisGMA, UDMA (urethane dimethacrylate), TEGDMA (triethyleneglycol dimethacrylate), and combination thereof.

The compositions described herein may include one or more curable components in the form of ethylenically unsaturated compounds with acid functionality. Such components contain acidic groups and ethylenically unsaturated groups in a single molecule. When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl(meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components. Also monomers, oligomers, and polymers of unsaturated carbonic acids such as (meth)acrylic acids, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler.

The curable dental compositions can include at least 1 wt-%, at least 3 wt-%, or at least 5 wt-% ethylenically unsaturated compounds with acid functionality, based on the total weight of the unfilled composition. The compositions can include at most 80 wt-%, at most 70 wt-%, or at most 60 wt-% ethylenically unsaturated compounds with acid functionality.

The curable dental compositions may include glass ionomer cements such as conventional glass ionomer cements that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers (i.e., glass ionomer cements) typically are supplied in powder/liquid formulations that are mixed just before use. The mixture will undergo self-hardening in the dark due to an ionic reaction between the acidic repeating units of the polycarboxylic acid and cations leached from the glass.

The glass ionomer cements preferably include resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of the acidic repeating units with pendent curable groups and a photoinitiator is added to provide a second cure mechanism, e.g., as described in U.S. Pat. No. 5,130,347 (Mitra). Acrylate or methacrylate groups are usually employed as the pendant curable group. In another type of RMGI, the cement includes a polycarboxylic acid, an acrylate or methacrylate-functional monomer and a photoinitiator, e.g., as in Mathis et al., "Properties of a New Glass Ionomer/ Composite Resin Hybrid Restorative", Abstract No. 51, J. Dent Res., 66:113 (1987) and as in U.S. Pat. No. 5,063,257 (Akahane et al.), U.S. Pat. No. 5,520,725 (Kato et al.), U.S. Pat. No. 5,859,089 (Qian), U.S. Pat. No. 5,925,715 (Mitra) and U.S. Pat. No. 5,962,550 (Akahane et al.). In another type of RMGI, the cement may include a polycarboxylic acid, an acrylate or methacrylate-functional monomer, and a redox or other chemical cure system, e.g., as described in U.S. Pat. No. 5,154,762 (Mitra et al.), U.S. Pat. No. 5,520,725 (Kato et al.), and U.S. Pat. No. 5,871,360 (Kato). In another type of RMGI, the cement may include various monomer-containing or resin-containing components as described in U.S. Pat. No. 4,872,936 (Engelbrecht), U.S. Pat. No. 5,227,413 (Mitra), U.S. Pat. No. 5,367,002 (Huang et al.), and U.S. Pat. No. 5,965,632 (Orlowski). RMGI cements are typically formulated as powder/liquid or paste/paste systems, and contain water as mixed and applied. The compositions are able to harden in the dark due to the ionic reaction between the acidic repeating units of the polycarboxylic acid and cations leached from the glass, and commercial RMGI products typically also cure on exposure of the cement to light from a dental curing lamp. RMGI cements that contain a redox cure system and that can be cured in the dark without the use of actinic radiation are described in U.S. Pat. No. 6,765,038 (Mitra).

An initiator is typically added to the (e.g. multifunctional) polymerizable ionic liquid or to the mixture of polymerizable ingredients comprising at least one (e.g. multifunctional) polymerizable ionic liquid, as described herein. The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

In some embodiments, the (e.g. multifunctional) polymerizable ionic liquid or composition comprising such is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition. In some embodiments, the curable dental composition may be irradiated with ultraviolet (UV) rays. For this embodiment, suitable photoinitiators include those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Hardening is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The (e.g. multifunctional) polymerizable ionic liquid or compositions comprising such may be chemically hardenable, i.e., the compositions contain a chemical initiator (i.e., initiator system) that can polymerize, cure, or otherwise harden the composition without dependence on irradiation with actinic radiation. Such chemically hardenable (e.g., polymerizable or curable) composition are sometimes referred to as "self-cure" compositions and may include redox cure systems, thermally curing systems and combinations thereof. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

Curable dental compositions can also be cured with a thermally or heat activated free radical initiator. Typical thermal initiators include peroxides such as benzoyl peroxide and azo compounds such as azobisisobutyronitrile.

In some embodiments, such as when the dental composition is employed as a dental restorative (e.g. dental filling or crown) or an orthodontic adhesive, the dental composition typically comprises appreciable amounts of (e.g. nanoparticle) filler. Such compositions preferably include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

In such dental compositions comprising appreciable amounts of filler, the one or more (e.g. multifunctional) polymerizable ionic liquids are typically present in an amount totaling at least 5 wt-%, 6 wt-%, 7 wt-%, 8 wt-%, 9 wt-%, or 10 wt-%, based on the total weight of the composition. The concentration of (e.g. multifunctional) polymerizable ionic liquids is generally no greater than about 60 wt-%. In some embodiments the total amount of (e.g. multifunctional) polymerizable ionic liquids is at most 40 wt-%, preferably at most 30 wt-%, and more preferably at most 25 wt-%.

Preferred dental compositions exhibit at least comparable or improved properties to commercially available hardenable dental compositions (as determined by the test methods described in the examples). The dental primer, adhesive, sealant, and combinations thereof exhibit a bond strength to enamel or dentin of at least 5 MPa or 10 MPa and in some embodiments a bond strength to enamel or dentin of at least 15 MPa or 20 MPa. The dental composite materials typically exhibit a diametral tensile strength (DTS) of at least 70, 75, or 80 MPa and a Barcol Hardness of at least 80 or 85. In some embodiments, the dental composite materials exhibit a DTS of at least 90 or 100 MPa. Further, the Watts shrinkage is typically less than 2%.

For embodiments wherein the (e.g. multifunctional) polymerizable ionic liquid is employed as an adhesive or cement, the amount of (e.g. multifunctional) polymerizable ionic liquid(s) can be considerably higher. For example, a (e.g. multifunctional) polymerizable ionic that is a liquid at 25° C., may be employed as the sole polymerizable component.

Dental compositions suitable for use as dental adhesives can also include filler in amount of at least 1 wt-%, 2 wt-%, 3 wt-%, 4 wt-%, or 5 wt-% based on the total weight of the composition. For such embodiments, the total concentration of filler is at most 40 wt-%, preferably at most 20 wt-%, and more preferably at most 15 wt-% filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Non-acid-reactive inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911 (Kangas et al.), and U.S. Pat. No. 7,649,029 (Kolb et al.).

Examples of suitable organic filler particles include filled or unfilled pulverized polycarbonates, polyepoxides, poly (meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E.I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO 1041.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin. Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like.

Suitable copolymerizable organometallic compounds may have the general formulas: $CH_2\!=\!C(CH_3)_m Si(OR)_n$ or $CH_2\!=\!C(CH_3)_m C\!=\!OOASiOR)_n$; wherein m is 0 or 1, R is an alkyl group having 1 to 4 carbon atoms, A is a divalent organic linking group, and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers or after mixing. It is typically preferred to combine the organosilane surface treatment compounds with nanoparticles before incorporation into the resin. The required amount of surface modifier is dependant upon several factors such as particle size, particle type, modifier molecular wt, and modifier type. In general it is preferred that approximately a monolayer of modifier is attached to the surface of the particle.

The surface modified nanoparticles can be substantially fully condensed. Fully condensed nanoparticles (with the exception of silica) typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Condensed crystalline (e.g. zirconia) nanoparticles have a high refractive index whereas amorphous nanoparticles typically have a lower refractive index.

In some embodiments, the dental compositions can have an initial color remarkably different than the cured dental structures. Color can be imparted to the composition through the use of a photobleachable or thermochromic dye. As used herein, "photobleachable" refers to loss of color upon exposure to actinic radiation. The composition can include at least 0.001 wt-% photobleachable or thermochromic dye, and typically at least 0.002 wt-% photobleachable or thermochromic dye, based on the total weight of the composition. The composition typically includes at most 1 wt-% photobleachable or thermochromic dye, and more typically at most 0.1 wt-% photobleachable or thermochromic dye, based on the total weight of the composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. The photobleachable dye is generally at least partially soluble in a hardenable resin.

Photobleachable dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change can be initiated by actinic radiation such as provided by a dental curing light which emits visible or near infrared (IR) light for a sufficient amount of time. The mechanism that initiates the color change in the compositions may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. Dental adhesives are also hardened by curing after applying the dental composition to the tooth. The method of treating an oral surface may comprise providing a dental article and adhering the dental article to an oral (e.g. tooth) surface. The dental article may comprise a cured composition comprising a polymerizable ionic liquid as described herein. Alternatively, the dental article may be a conventional dental article (without a polymerizable ionic liquid) adhered with a conventional primer (without a polymerizable ionic liquid) and an adhesive comprising a polymerizable ionic liquid; a primer comprising a polymerizable ionic liquid and a conventional adhesive (without a polymerizable ionic liquid); or both a primer and adhesive, each comprising a polymerizable ionic liquid.

In other embodiments, the compositions can be hardened (e.g., polymerized) into dental articles prior to applying. For example, a dental article such as a crown may be preformed from the hardenable dental composition described herein. Dental composite (e.g. crowns) artilces can be made from the curable composition described herein by casting the curable composition in contact with a mold and curing the composition. Alternatively, dental composite (e.g. crowns) article can be made by first curing the composition forming a mill bland and then mechanically milling the composition into the desired article.

Another method of treating a tooth surface comprises providing a dental composition as described herein wherein the composition is in the form of a (partially hardened) hardenable, self-supporting, malleable structure having a first semi-finished shape; placing the hardenable dental composition on a tooth surface in the mouth of a subject; customizing the shape of the hardenable dental composition; and hardening the hardenable dental composition. The customization can occur in the patient's mouth or on a model outside the patient mouth such as described in U.S. Pat. No. 7,674,850 (Karim et al.); incorporated herein by reference.

Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

EXAMPLES

| Abbreviation | Chemical Description (Supplier, Location) |
|---|---|
| \multicolumn{2}{c}{Polymerizable Monomer} | |
| BisGMA | 2,2-bis[4-(2-hydroxy-3-methacryloyloxypropoxy)phenyl]propane |
| Bis EMA6 | ethoxylated bisphenol A methacrylate as further described in U.S. Pat. No. 6,030,606 available from Sartomer as "CD541" |
| TEGDMA | triethyleneglycol dimethacrylate |
| HEMA | 2-Hydroxyethyl methacrylate (Sigma-Aldrich, St. Louis, MO) |
| UDMA | Diurethane dimethacrylate (CAS No. 41137-60-4), commercially available as Rohamere 6661-0 (Rohm Tech, Inc., Malden, MA) |
| VBCP | Polymer made by reacting AA: ITA copolymer with sufficient IEM to convert 16 mole percent of the acid groups of the copolymer to pendent methacrylate groups according to the dry polymer preparation of Example 11 of U.S. Pat. No. 5,130,347. |

-continued

| Abbreviation | Chemical Description (Supplier, Location) |
|---|---|
| | Inorganic Fillers |
| S/T TiO$_2$ filler | Silane treated TiO$_2$ filler:<br>The pH of an acetic acid water solution was adjusted to slightly less than 2.0 by adding 1.47 parts of acetic acid into 1.47 parts of DI water at room temperature. This solution was slowly added to 4.37 parts of methacryloxypropyltrimethoxy silane (available from GE Silicones under the trade designation "Silquest A-174") and 4.37 parts of methanol solution with stirring, stirring the solution for one hour. To this solution was added 96 parts of Ti Pure R-960 Titanium Dioxide from Dupont and 1.71 parts of Aerosil R-972 from Degussa, and mixed vigorously for about 10 minutes. The mixture was dried at 115° C. for 4 hours, crushed, and screened through a 74 micron nylon screen. |
| R812S Filler | Hydrophobic fumed silica available from Degussa Evonik Industries, Parsippany, NJ, under the trade designation "Aerosil Fumed Silica R812S". |
| Zr/Si Filler | One hundred parts zirconia silica filler of average particle size 0.6-0.9 micrometers was mixed with deionized water at a solution temperature of between 20-30° C., and the pH is adjusted to 3-3.3 with trifluoroacetic acid (0.278 parts). The A-174 silane was added to the slurry in an amount 7 parts and the blend is mixed over 2 hours. At the end of 2 hours, the pH is neutralized with calcium hydroxide. The filler is dried, crushed and screened through a 74 or 100 micron screen. |
| Zr/Si Nano-Cluster Filler | Refers to silane-treated zirconia/silica nanocluster filler prepared essentially as described in U.S. Pat. No. 6,730,156 (Preparatory Example A (line 51-64) and Example B (column 25 line 65 through column 26 line 40). |
| 20 nm Si Nanomer Filler | Refers to silane-treated nano-sized silica having a nominal particle size of approximately 20 nanometers, prepared essentially as described in U.S. Pat. No. 6,572,693 B1, (column 21, lines 63-67 for Nanosized particle filler, Type #2. |
| | Components of Photointiator Package |
| BHT | 2,6-di-tert-butyl-4-methylphenol (Sigma-Aldrich Fine Chemicals, St. Louis, MO) |
| CPQ | camphorquinone (Sigma-Aldrich) |
| DPIHFP | "DPIHFP" refers to diphenyl iodonium hexafluorophosphate; |
| EDMAB | ethyl 4-(N,N-dimethylamino)benzoate (Sigma-Aldrich) |

Synthesis of Polymerizable Ionic Liquids
Preparation of "PIL A1"

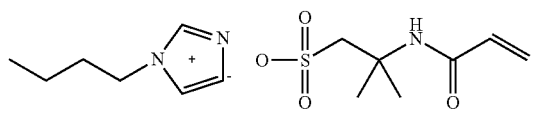

Butyl imidazole (4.82 g, 0.04 mol), BHT (0.015 g), and methanol (50 mL) were mixed with in a flask equipped with magnetic stirring. 2-acrylamido-2-methyl-1-propanesulfonic acid (8.05 g, 0.04 mol) and methanol (50 mL) were added at room temperature. The acid dissolved completely in 30 minutes. The reaction was stirred at room temperature overnight. The solvent was then removed under vacuum to give a viscous liquid.

Preparation of "PIL A2"

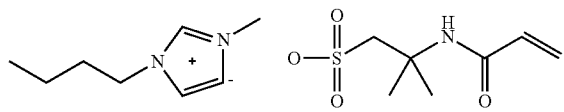

1-butyl-3-methylimidazolium hydrogen carbonate (Aldrich, 50% solution in methanol:water (2:3), 16 g, 0.04 mol), BHT (0.010 g), and methanol (20 mL) were mixed in a flask equipped with magnetic stirring. 2-acrylamido-2-methyl-1-propanesulfonic acid (8.28 g, 0.04 mol) and methanol (60 mL) were added while cooling the flash with a room temperature water bath. Carbon dioxide was generated and the mixture became clear. The reaction was stirred at room temperature for 4 hours. The solvent methanol and water was removed under vacuum to give a viscous liquid.

Preparation of PIL B

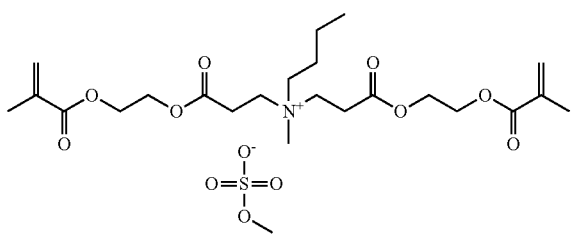

A mixture of n-butylamine (0.993 g, 14 mmol, Aldrich) and methacryloxyethyl acrylate (5.00 g, 27 mmol, prepared according to Klee, J. E., et. al., *Macromol. Chem. Phys.,* 200, 1999, 517) was stirred at room temperature for 24 hours. The intermediate product was a colorless liquid.

Dimethyl sulfate (0.57 g, 4.5 mmol) was added to the intermediate product from above (2.00 g, 4.5 mmol) dropwise over 10 minutes. The mixture was stirred for 17 hours to give the final PIL product as a thick liquid.

Preparation of PIL-C ("POS-2")
Polymerizable Onium Salt 2 (POS-2): represented by the following formula:

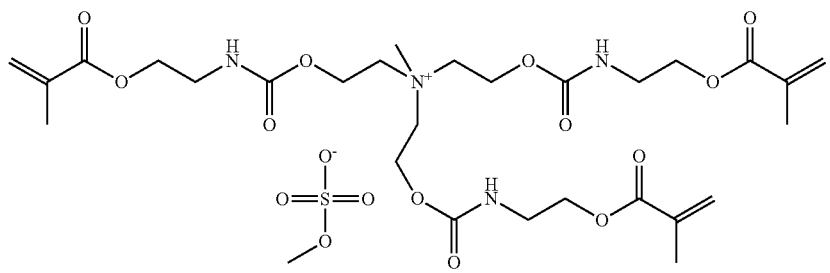

To a solution of tris-(2-hydroxyethyl)methylammonium methylsulfate (11.58 g, 0.04 mol, available from BASF), isocyanatoethyl methacrylate (19.58 g, 0.12 mol), and 2,6-di-tert-butyl-4-methylphenol (BHT, 0.020 g, available from Aldrich) in methylene chloride (50 mL) in a flask fitted with a drying tube and a magnetic stirrer was added a drop of dibutyltin dilaurate. The solution was cooled in an ice bath and stirred for 3 hours, then allowed to warm to room temperature and stirring was continued for another 36 hours. Progress of the reaction was monitored by infrared spectroscopy, observing the disappearance of the isocyanate absorption. When reaction was complete the solvent was removed at reduced pressure yielding a very viscous liquid.

Preparation of PIL D

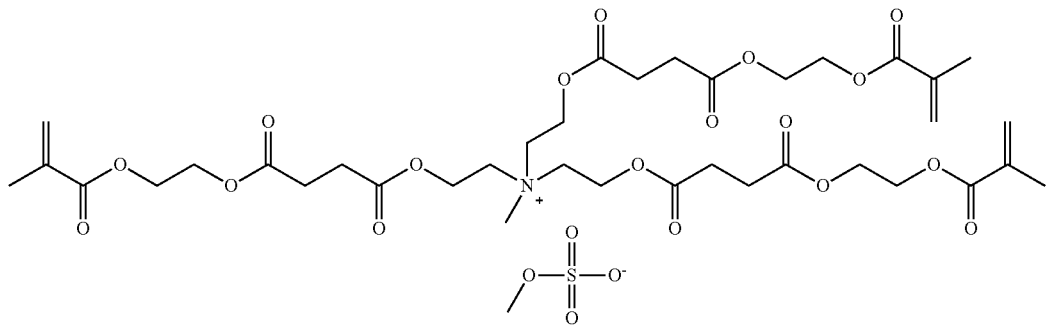

To a stirred, ice cooled solution of tris-(2-hydroxyethyl)methylammonium methylsulfate (17.38 g, 0.06 mol), mono-2-(methacryloyloxy)ethyl succinate (41.42 g, 0.18 mol, available from Aldrich), and 4-dimethylaminopyridine (1.098 g, 0.009 mol, available from Aldrich) in ethyl acetate (150 mL) was added dropwise over a 2 hour period a solution of 1,3-dicyclohexylcarbodiimide (DCC, 37.1 g, 0.18 mol, available from Aldrich) in ethyl acetate (150 mL). After the DCC solution was added, the temperature of the reaction mixture was allowed to rise gradually to room temperature, and then the reaction was stirred for 14 hours. Then 0.5 g of deionized water and 2.0 g of silica gel were added into the flask and the reaction mixture stirred for 1 hour. The mixture was then filtered and solvent removed from the filtrate at reduced pressure to yield a very viscous liquid product having a slight yellow color.

Preparation of PIL E

Into a vial was placed 1.000 g (6.2 mmol) of N,N-dimethyl vinyl benzylamine (mixture of isomers, Aldrich) and 1.726 g (6.2 mmol) mono-(methacryloxy)ethyl phthalate (Aldrich). After mixing for 5 minutes a liquid product was obtained.

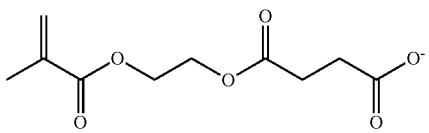

-continued

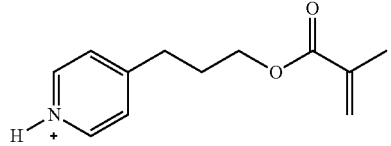

Into a flask was placed 71.14 g (0.52 mol) 4-hydroxypropyl pyridine (Aldrich) and 0.50 g phenothiazine (Aldrich). Methacrylic anhydride (95.09 g, 0.62 mol, Aldrich) was added dropwise over 2 hours. The temperature reached 50° C. during the addition. The mixture was stirred overnight at room temperature. Ethyl acetate (300 mL) was added and the mixture was washed with a solution of sodium hydroxide (30 g) in water (300 mL). The organic phase was concentrated to give a dark oil. Phenothiazine was added (0.30 g) and the oil was distilled. A yellow oil was collected at 108-111° C. @ 60 mTorr. (yield=55.71 g)

Into a vial was placed 4.028 g (19.6 mmol) of 4-methacryloxypropyl pyridine and 4.512 g (19.6 mmol) of mono-(methacryloxyethyl) succinate. The mixture was shaken for 10 minutes at room temperature to give the product as an orange oil.

Preparation of PIL F

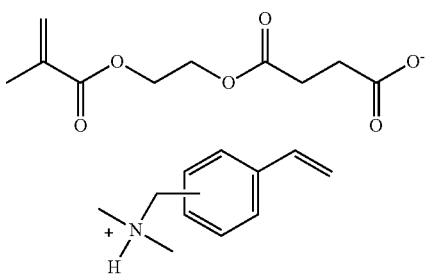

Into a vial was placed 1.000 g (6.2 mmol) of N,N-dimethyl vinyl benzylamine (mixture of isomers, Aldrich) and 1.428 g (6.2 mmol) mono-(methacryloxy)ethyl succinate (Aldrich). After mixing for 5 minutes the liquid product was obtained.

Preparation of PIL G

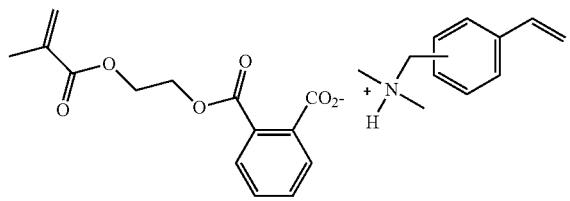

Into a vial was placed 1.000 g (6.2 mmol) of N,N-dimethyl vinyl benzylamine (mixture of isomers, Aldrich) and 1.726 g (6.2 mmol) mono-(methacryloxy)ethyl phthalate (Aldrich). After mixing for 5 minutes a liquid product was obtained.

Preparation of PIL H

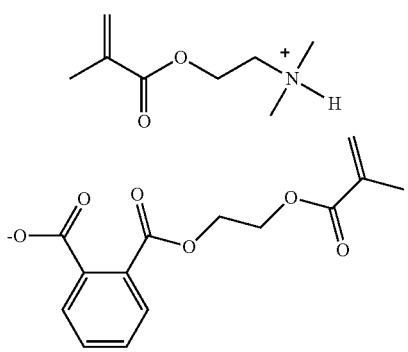

A mixture of dimethylaminoethyl methacrylate (56.62 g, 0.36 mol), Prostab 5198 (17 mg), and mono-2-(methacryloxy)ethyl phthalate (Aldrich, 100.00 g, 0.36 mol) was placed in a jar. The jar was capped and rolled at room temperature for 17 hours. A colorless oil was obtained.

Preparation of PIL I

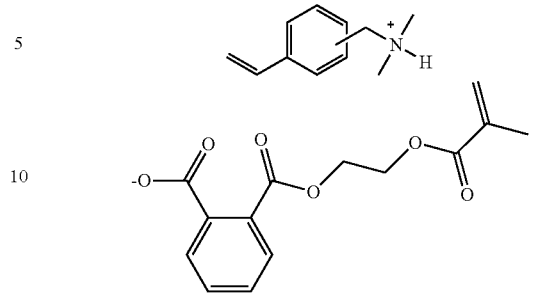

A mixture of N,N-dimethyl vinyl benzylamine (mixture of isomers, Aldrich, 1.000 g, 6.2 mmol) and mono-2-(methacryloxy)ethyl phthalate (1.726 g (6.2 mmol) was placed in a vial. After mixing for 5 minutes a liquid product was obtained.

Determination of Air to Nitrogen Curing Exotherm Ratio:

The photo polymerization behavior of monomers under N2 and air was examined using differential scanning photocalorimetry (photo DSC). The photo DSC was a TA instrument (New Castle, Del.) with DSC module 2920. The light source was a mercury/argon lamp with an Oriel PN 59480 425 nm long pass light filter. The light intensity was 3 mW/cm$^2$, measured using an International Light light meter Model IL 1400 equipped with a Model XRL, 340A detector. The photo curable samples contained 0.5% camphorquinone (Sigma-Aldrich), 1.0% ethyl 4-(N,N-dimethylamino)benzoate (Sigma-Aldrich) and 1.0% diphenyl iodium hexafluorophosphate as the photoinitiator package. A 10 mg cured sample was used as a reference.

About 10 mg of the sample was weighed accurately for the testing with a Hermetic Pan (aluminum sample pan) as the sample holder. The samples were equilibrated at 37° C. for 5 minutes, and then the light aperture was opened to irradiate the sample. During irradiation the sample temperature was held at 37° C. The total irradiation time was 30 minutes. After 30 minutes, the aperture was closed and the sample maintained at 37° C. for another 5 minutes. The samples were tested under nitrogen and air atmosphere respectively.

The data was collected as heat output per unit weight (mW/g). The data was analyzed using TA Thermal Solutions Universal Analysis software.

Monomers were run once under nitrogen, then an identical sample was run under air. The DSC recorded the heat generation from the curing sample during exposure, and the area under the curve was integrated to give total Joules/gram of the monomer. The heat generated when the sample was cured in air was divided by the heat generated when the sample was cured in nitrogen to give the curing ratio. A higher ratio represents less oxygen inhibition.

Testing Results for Photocuring a Monofunctional PIL and 2-Hydroxyethyl Methacrylate (HEMA, Available from Aldrich) by Photo DSC

|  | Curing ratio (air/N$_2$) |
|---|---|
| 90 wt % PIL-A/10 wt % HEMA | 0.90 |
| 80 wt % PIL-A/20 wt % HEMA | 0.89 |
| 70 wt % PIL-A/30 wt % HEMA | 0.87 |
| 60 wt % PIL-A/40 wt % HEMA | 0.88 |
| 50 wt % PIL-A/50 wt % HEMA | 0.84 |
| 40 wt % PIL-A/60 wt % HEMA | 0.58 |
| 30 wt % PIL-A/70 wt % HEMA | 0.46 |

-continued

| | Curing ratio (air/N$_2$) |
|---|---|
| 20 wt % PIL-A/80 wt % HEMA | 0.35 |
| 10 wt % PIL-A/90 wt % HEMA | 0.25 |

Testing Results for Photocuring a Multifunctional PIL and Triethylene Glycol Dimethacrylate (TEGDMA, Available from Aldrich) by Photo DSC

| | Curing ratio (air/N$_2$) |
|---|---|
| 100 wt % PIL-C | 0.97 |
| 90 wt % PIL-C/10 wt % TEGDMA | 0.95 |
| 80 wt % PIL-C/20 wt % TEGDMA | 0.93 |
| 70 wt % PIL-C/30 wt % TEGDMA | 0.94 |
| 60 wt % PIL-C/40 wt % TEGDMA | 0.90 |
| 50 wt % PIL-C/50 wt % TEGDMA | 0.84 |
| 40 wt % PIL-C/60 wt % TEGDMA | 0.79 |
| 30 wt % PIL-C/70 wt % TEGDMA | 0.78 |
| 20 wt % PIL-C/80 wt % TEGDMA | 0.60 |
| 10 wt % PIL-C/90 wt % TEGDMA | 0.40 |
| 100 wt % TEGDMA | 0.36 |

Testing Results for Photocuring a Multifunctional Pil Comprising a Polymerizable Cation and Polymerizable Antion by Photo DSC

| | Curing ratio (air/N$_2$) |
|---|---|
| 100 wt % PIL-F | 0.79 |
| 100 wt % PIL-G | 0.94 |
| 100 wt % PIL-H | 0.97 |

Test Method for Evaluating Bond Strength of Dental Primer, Dental Adhesive and Dental Sealant to Dental Hard Tissues Potted bovine teeth were ground using 120 grit sand paper to expose enamel or dentin, then teeth were further polished using 320 grit sand paper to smooth the surface. The bovine tooth surface was dried by applying a stream of compressed air for 3 seconds, then a drop of primer was applied, scrubbed for 20 seconds, dried by a stream of compressed air for 20 seconds, followed by application of a thin layer of adhesive (the adhesive composition is described below) with scrubbing for 20 seconds. The primer and adhesive combination was then cured for 20 seconds with a dental blue curing (3M ESPE Elipar Freelight 2) for 20 seconds. Previously prepared molds made from a 2.5-mm thick "Teflon" sheet with a 4.7 mm diameter hole through the sheet were clamped to each prepared tooth so that the central axis of the hole in the mold was normal to the tooth surface. The hole in each mold was filled with a visible light-curable dental restorative (available from 3M ESPE as "Filtek™ Z250 Restorative" A2 shade) and cured for 20 seconds irradiation with the dental curing light. The teeth and molds were allowed to stand for about 5 minutes at room temperature, then stored in distilled water at 37° C. for 24 hours unless otherwise noted. The molds were then carefully removed from the teeth, leaving a molded button of restorative attached to each tooth.

The adhesive strength was evaluated utilizing the wire loop method by mounting the acrylic disk in a holder clamped in the jaws of an "Instron 1123" apparatus with the polished tooth surface oriented parallel to the direction of pull. A loop of orthodontic wire (0.44 mm diameter) was placed around the restorative button adjacent to the polished tooth surface. The ends of the orthodontic wire were clamped in the pulling jaw of the Instron apparatus, thereby placing the bond in shear stress. The bond was stressed until it (or the dentin or button) failed using a crosshead speed of 2 mm/min. Five adhesion samples were prepared for each set of primer and adhesive.

Self Etching Primer

Control Primer A

| Component | Wt-% |
|---|---|
| Maleic Acid | 10 |
| HEMA | 45 |
| Water | 45 |
| Total | 100.0 |

Control Primer B

| Component | Wt-% |
|---|---|
| Maleic Acid | 10 |
| HEMA | 15 |
| Water | 75 |
| Total | 100.0 |

| Control Dental Adhesive | | |
|---|---|---|
| Component | Wt-% solids | Weight, g |
| bisGMA | 53.7 | 2.2 |
| HEMA | 34.1 | 1.4 |
| TEGDMA | 9.8 | 0.4 |
| CPQ | 0.5 | 0.02 |
| EDMAB | 1.0 | 0.04 |
| DPIHFP | 1.0 | 0.04 |
| total | 100 | 4.10 |

Example 1

Dental Primer

| Component | Wt-% |
|---|---|
| Maleic Acid | 10 |
| PIL A2 | 45 |
| Water | 45 |
| Total | 100.0 |

Example 2

Dental Primer

| Component | Wt-% |
|---|---|
| Maleic Acid | 10 |
| PIL A2 | 25 |
| Water | 65 |
| Total | 100.0 |

Example 3

Dental Primer

| Component | Wt-% |
|---|---|
| Maleic Acid | 10 |
| PIL A1 | 15 |
| Water | 75 |
| Total | 100.0 |

Example 4

Dental Primer

| Component | Wt-% |
|---|---|
| Maleic Acid | 10 |
| PIL A1 | 45 |
| Water | 45 |
| Total | 100.0 |

The test results of utilizing dental primers comprising a polymerizable ionic liquid (Examples 1-4) in combination with a conventional dental adhesive (Control Dental Adhesive), without a polymerizable ionic liquid were as follows:

Dentin Results:

| Primer and Control Adhesive | Bond strength (MPa) | Std. Dev. |
|---|---|---|
| Example 1—Primer | 17.4 | 5.2 |
| Control Primer A | 10.1 | 2.5 |

Enamel Results:

| Primer and Control Adhesive | Bond strength (MPa) | Std. Dev. |
|---|---|---|
| Example 2—Primer | 12.7 | 3.3 |
| Control Primer A | 11.9 | 3.0 |

Enamel Results:

| Primer and Control Adhesive | Bond strength (MPa) | Std. Dev. |
|---|---|---|
| Example 3—Primer | 13.0 | 0.9 |
| Control Primer B | 9.0 | 1.0 |

Dentin Results:

| Primer and Control Adhesive | Bond strength (MPa) | Std. Dev. |
|---|---|---|
| Example 4 | 13.6 | 2.1 |
| Control Primer A | 9.3 | 0.7 |

Example 5

Dental Adhesive

| Component | Wt-% Solids | Weight, g |
|---|---|---|
| PIL-C | 68.3 | 1.4 |
| HEMA | 0.0 | 0 |
| TEGDMA | 29.3 | 0.6 |
| CPQ | 0.5 | 0.01 |
| EDMAB | 1.0 | 0.02 |
| DPIHFP | 1.0 | 0.02 |
| total | 100 | 2.05 |

The test results of utilizing a conventional dental primer (Control Primer A), without a polymerizable ionic liquid in combination with a dental adhesive (Example 5), comprising a polymerizable ionic liquid were as follows:

| | Enamel Bond Strength (MPa) | Std. Dev. | Dentin Bond Strength (MPa) | Std. Dev. |
|---|---|---|---|---|
| Control Dental Adhesive | 11.6 | 4.3 | 10.9 | 2.3 |
| Example 5 | 14.3 | 3.9 | 13.9 | 3.1 |

Example 6

Dental Adhesive

| Component | Wt-% Solids | Weight, g |
|---|---|---|
| PIL C | 9.8 | 0.2 |
| HEMA | 0.00 | 0 |
| TEGDMA | 87.8 | 1.8 |
| CPQ | 0.5 | 0.01 |
| EDMAB | 1.0 | 0.02 |
| DPIHFP | 1.0 | 0.02 |
| Total | 100 | 2.05 |

Using Primer Example 4 as the primer, the dental adhesive of Example 6, (i.e. containing PIL C) was evaluated in the same manner as previously described and compared to the Control Dental Adhesive.

| | Enamel Bond Strength (MPa) | Std. Dev. | Dentin Bond Strength (MPa) | Std. Dev. |
|---|---|---|---|---|
| Example 6 | 18.6 | 3 | 21.2 | 1.2 |
| Control Dental Adhesive | 15.8 | 5.8 | 13.4 | 2.1 |

The results show that the highest bond strength was achieved with a polymerizable ionic liquid based primer in combination with a polymerizable ionic liquid based adhesive.

Control Dental Sealant

| Component | Wt-% Solids | Weight, g |
|---|---|---|
| BisGMA | 46.35 | 2.00 |
| TEGDMA | 46.35 | 2.00 |

Example 7

Dental Sealant

| Component | Wt-% Solids | Weight, g |
|---|---|---|
| PIL C | 74.16 | 3.2 |
| TEGDMA | 18.54 | 0.8 |
| CPQ | 0.23 | 0.01 |
| EDMAB | 1.16 | 0.05 |
| DPIHFP | 0.58 | 0.025 |
| S/T TiO2 Filler | 0.70 | 0.03 |
| R812S Filler | 4.63 | 0.20 |
| Total | 100 | 4.32 |

Example 8

Dental Sealant

| Component | Wt-% Solids | Weight, g |
|---|---|---|
| PIL D | 74.16 | 3.2 |
| TEGDMA | 18.54 | 0.8 |
| CPQ | 0.23 | 0.01 |
| EDMAB | 1.16 | 0.05 |
| DPIHFP | 0.58 | 0.025 |
| S/T TiO2 Filler | 0.70 | 0.03 |
| R812S Filler | 4.63 | 0.20 |
| Total | 100 | 4.32 |

| | Enamel Bond Strength (MPa) | Std. Dev. | Curing ratio (air/nitrogen) |
|---|---|---|---|
| Example 7 | 16.0 | 2.9 | 0.96 |
| Example 8 | 15.2 | 1.1 | 0.88 |
| Control Sealant | 13.2 | 2.8 | 0.71 |

Test Methods for Evaluating Composite:

Watts Shrinkage Test Method

The Watts Shrinkage (Watts) Test Method measures shrinkage of a test sample in terms of volumetric change after curing. The sample preparation (90-mg uncured composite test sample) and test procedure were carried out as described in the following reference: Determination of Polymerization Shrinkage Kinetics in Visible-Light-Cured Materials: Methods Development, Dental Materials, October 1991, pages 281-286. Results in terms of percent shrinkage were reported as the average of three replicates for each sample.

Barcol Hardness Test Method

Barcol Hardness of a test sample was determined according to the following procedure. An uncured composite sample was cured in 2.5-mm thick TEFLON mold sandwiched between a sheet of polyester (PET) film and a glass slide for 30 seconds and cured with an ELIPAR Freelight 2 dental curing light (3M Company). After irradiation, the PET film was removed and the hardness of the sample at both the top and the bottom of the mold was measured using a Barber-Coleman Impressor (a hand-held portable hardness tester; Model GYZJ 934-1; Barber-Coleman Company, Industrial Instruments Division, Lovas Park, Ind.) equipped with an indenter. Top and bottom Barcol Hardness values were measured at 5 minutes after light exposure. Results were reported as the average of three measurements.

Diametral Tensile Strength (DTS) Test Method

DTS of a test sample was prepared according to the following procedure. An uncured sample was injected into a 4-mm (inside diameter) glass tube that was capped with silicone rubber plugs; and then the tube was compressed axially at approximately 2.88 kg/cm$^2$ pressure for 5 minutes. The sample was then light cured for 80 seconds by exposure to a XL 1500 dental curing light (3M Company, St. Paul, Minn.), followed by irradiation for 90 seconds in a Kulzer UniXS curing box (Heraeus Kulzer GmbH, Germany). Cured samples were allowed to stand for 1 hour at about 37° C./90%+Relative Humidity and then were cut with a diamond saw to form 8-mm long cylindrical plugs for measurement of compressive strength. The plugs were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Five cylinders of cured samples were prepared and measured with the results reported in MPa as the average of the five measurements.

For each of the following experiments, the Control Dental Composite was a commercially available dental material available from 3M ESPE under the trade designation "Filtek™ Z250 Restorative".

Example 9

Dental Composite

| | Wt-% Total Composition | Wt-% of Resin | Weight - grams |
|---|---|---|---|
| Part A—Resin Component | | | |
| PIL C | 12.636 | 63.18 | 3.1590 |
| UDMA | 4 | 20 | 1.0000 |
| TEGDMA | 3 | 15 | 0.7500 |
| CPQ | 0.034 | 0.17 | 0.0085 |
| EDMAB | 0.2 | 1 | 0.0500 |
| DPIHFP | 0.1 | 0.5 | 0.0250 |
| BHT | 0.03 | 0.15 | 0.0075 |
| Part B Zr/Si filler | 80 | NA | 20 |
| Total | 100 | 100 | 25 |

The methacrylates monomers, polymerizable ionic liquids C, photoinitiator, and BHT were mixed in a medium cup. Zr/Si filler (13 g) was added and mixed for 3 minutes at a mixing speed of 3500 rpm. The mixture was allowed to cool down and an additional 5.0 g of Zr/Si filler was added and mixed at 3500 rpm for 1.5 minutes. The mixture was allowed to cool down again and then 1 g of Zr/Si filler was added and mixed at 3500 rpm for 1.5 minutes. After cooling, 1.0 g of Zr/Si filler was added and speed mixed at 3500 rpm for 1.5 minutes. After cooling, it was speed mixed further for 1.5 minutes to give the final paste.

|  | DTS (MPa) | Std. Dev. | Shrinkage (%) | Std. Dev. | Hardness | Std. Dev. | Curing ratio (air/nitrogen) |
|---|---|---|---|---|---|---|---|
| Example 9 | 90.2 | 8.8 | 2.3 | 0.03 | 82.7 | 0.6 | 0.99 |
| Control Dental Composite | 90.9 | 10.4 | 2.1 | 0.05 | 83.5 | 1.4 | 0.85 |

Example 10

Dental Composite

|  | Wt-% Total Composition | Wt-% Resin | Weight grams |
|---|---|---|---|
| Part A—Resin Component |  |  |  |
| PIL D | 13.08 | 68.18 | 3.4 |
| BisEMA6 | 5.77 | 30.00 | 1.5 |
| CPQ | 0.03 | 0.17 | 0.009 |
| EDMAB | 0.10 | 1.00 | 0.025 |
| DPIHFP | 0.19 | 0.50 | 0.05 |
| BHT | 0.03 | 0.15 | 0.008 |
| Part B—Zr/Si filler | 80.77 | NA | 21 |
| Total | 100 | 100 | 26 |

Example 11

Dental Composite

|  | Wt-% Total Composition | Wt-% Resin | grams |
|---|---|---|---|
| Part A—Resin Component |  |  |  |
| PIL D | 20.45 | 98.18 | 4.909 |
| CPQ | 0.04 | 0.17 | 0.0085 |
| EDMAB | 0.10 | 0.50 | 0.025 |
| DPIHFP | 0.21 | 1.00 | 0.05 |
| BHT | 0.03 | 0.15 | 0.0075 |
| Part B—Zr/Si filler | 79.17 | NA | 19 |
| Total | 100 | 100 | 24 |

|  | DTS (MPa) | Std. Dev. | Shrinkage, vol % | Std. Dev. | Hardness | Std. Dev. |
|---|---|---|---|---|---|---|
| Example 10 | 92.3 | 5.5 | 1.84 | 0.03 | 86.2 | 1.3 |
| Example 11 | 85.6 | 5.2 | 1.84 | 0.02 | 87.6 | 1.1 |
| Control Dental Composite | 95.3 | 7.1 | 1.89 | 0.02 | 85.5 | 1.4 |

Example 12

Dental Composite

|  | Wt-% Total Composition | Wt-% Resin | grams |
|---|---|---|---|
| Part A—Resin Component |  |  |  |
| PIL D | 9.06 | 48.20 | 2.41 |
| UDMA | 8.46 | 45.00 | 2.25 |
| TEGDMA | 0.94 | 5.00 | 0.25 |
| CPQ | 0.03 | 0.17 | 0.0085 |
| EDMAB | 0.09 | 0.50 | 0.025 |
| DPIHFP | 0.19 | 1.00 | 0.05 |
| BHT | 0.03 | 0.15 | 0.0075 |
| Part B—Zr/Si filler | 81.20 | NA | 21.6 |
| Total | 100 | 100 | 26.6 |

|  | DTS (MPa) | Std. Dev. | Shrinkage (%) | Std. Dev. | Hardness | Std. Dev. |
|---|---|---|---|---|---|---|
| Example 12 | 104 | 4.5 | 2.0 | 0.04 | 85.3 | 1.6 |
| Control Dental Composite | 88.6 | 6.3 | 1.9 | 0.02 | 86.5 | 1.0 |

Example 13

Dental Composite

|  | Wt-% Total Composition | Wt-% Resin | grams |
|---|---|---|---|
| Part A—Resin Component |  |  |  |
| PIL D | 11.47 | 48.18 | 2.409 |
| UDMA | 8.57 | 36.00 | 1.8 |
| TEGDMA | 3.33 | 14.00 | 0.7 |
| CPQ | 0.04 | 0.17 | 0.0085 |
| EDMAB | 0.12 | 0.50 | 0.025 |
| DPIHFP | 0.24 | 1.00 | 0.05 |
| BHT | 0.04 | 0.15 | 0.0075 |
| Part B—20 nm silica nanomer filler | 7.62 | NA | 1.6 |
| Part B—Zr/Si nano cluster filler | 68.57 | NA | 14.4 |
| Total | 100 | 100 | 21.0 |

Liquid components were mixed at 3500 rpm for 2.5 minutes, and formed a clear solution. 1.0 g 20 nm silica nanomer filler and 9.0 g Si/Zr nano-cluster filler were mixed first, then added into the resin, speed mixed at 2000 rpm for 1 minute, then speed mixed at 3500 rpm for 2 minutes. 20 nm Si nanomer filler (0.3 g) and Si/Zr nano-cluster filler (2.97 g) were added, then speed mixed at 3500 rpm for 2 minutes. 20 nm Si nanomer filler (0.3 g) and Si/Zr nano-cluster filler (2.70 g) were added then speed mixed at 3500 rpm for 2 minutes, to give the final paste.

Control is Filtek™ Supreme Universal Restorative composite

|  | DTS (MPa) | Std. Dev. | Shrinkage | Std. Dev. |
| --- | --- | --- | --- | --- |
| Example 9 | 73.0 | 7.9 | 1.9 | 0.02 |
| Control Dental Composite | 81.1 | 3.3 | 1.9 | 0.02 |

Example 14

Resin Modified Glass Ionomer Restorative

| Part A—Resin Component | Wt-% Resin Component A | grams |
| --- | --- | --- |
| PIL E | 20 | 3.99 |
| DI Water | 30.1 | 6.02 |
| VBCP | 48.7 | 9.73 |
| CPQ | 0.21 | 0.042 |
| DPIHFP | 0.98 | 0.196 |
| BHT | 0.05 | 0.0098 |
| Total | 100 | 24 |

The organic components of Example 14 were mixed in a medium cup for five 2 minute cycles at 3500 rpm. This polymerizable liquid resin mixture was then hand mixed with a FAS glass powder (as described in U.S. Pat. No. 5,154,762) of "Vitremer™ Core Build-Up Materials Restorative" commercially available from 3M™ ESPE™ at a weight ratio 1 to 2.5 (powder).

A control was made in the same manner except that HEMA was used in place of PIL E.

|  | DTS (MPa) | Std Dev |
| --- | --- | --- |
| Example 14 | 48.2 | 4.69 |
| Control | 38.9 | 2.5 |

Example 15

Resin Modified Glass Ionomer Restorative

| Component | exp. Gram | Wt-% Resin Component A |
| --- | --- | --- |
| PIL F | 3.99 | 20.0 |
| DI water | 6.02 | 30.1 |
| VBCP | 9.73 | 48.7 |
| CPQ | 0.042 | 0.21 |
| DPIHFP | 0.196 | 0.98 |
| BHT | 0.0098 | 0.05 |
| total | 20.0 | 100 |

Example 16

Resin Modified Glass Ionomer Restorative

| Component | exp. Gram | Wt-% Resin Component A |
| --- | --- | --- |
| PIL G | 3.99 | 20.0 |
| DI water | 6.02 | 30.1 |
| VBCP | 9.73 | 48.7 |
| CPQ | 0.042 | 0.21 |
| DPIHFP | 0.196 | 0.98 |
| BHT | 0.0098 | 0.05 |
| total | 20.0 | 100 |

For Examples 15 and 16, organic components were added into a speed mixing cup respectively, and then mixed using 3000 rpm for 3 minutes. This was repeated 3 times. This polymerizable liquid resin mixture was then hand mixed with a FAS glass powder (as described in U.S. Pat. No. 5,154,762) of "Vitremer™ Core Build-Up Materials Restorative" commercially available from 3M™ ESPE™ at a weight ratio 1 to 2.5 (powder). A control was made in the same manner as Example 15 except that HEMA was used in place of PIL E. The control sample and Example 15 formed clear solutions, whereas Example 16 formed a slight cloudy solution.

|  | DTS (MPa) | Std Dev |
| --- | --- | --- |
| Example 15 | 51.1 | 3.9 |
| Example 16 | 48.1 | 2.8 |
| Control | 40.9 | 1.6 |

Example 17

Resin Modified Glass Ionomer Restorative

| Part A—Resin Component | grams | Wt-% Resin Component A | Wt-% of Total Composition |
| --- | --- | --- | --- |
| PIL H | 3.99 | 19.95 | 3.99 |
| DI Water | 6.02 | 30.1 | 6.02 |
| CPQ | 0.042 | 0.21 | 0.042 |
| VBCP | 9.73 | 48.65 | 9.73 |
| DPIHFP | 0.196 | 0.98 | 0.196 |
| BHT | 0.0098 | 0.049 | 0.0098 |

Example 18

Resin Modified Glass Ionomer Restorative

| Part A—Resin Component | grams | Wt-% Resin Component A | Wt-% of Total Composition |
| --- | --- | --- | --- |
| PIL I | 3.99 | 19.95 | 3.99 |
| DI Water | 6.02 | 30.1 | 6.02 |
| CPQ | 0.042 | 0.21 | 0.042 |
| VBCP | 9.73 | 48.65 | 9.73 |
| DPIHFP | 0.196 | 0.98 | 0.196 |
| BHT | 0.0098 | 0.049 | 0.0098 |

The organic resin component (Part A) of Examples 17 and 18 were each separately mixed in a medium cup for five 2 minute cycles at 3000 rpm. This polymerizable liquid resin mixture was then hand mixed with a FAS glass powder (as described in U.S. Pat. No. 5,154,762) of "Vitremer™ Core Build-Up Materials Restorative" commercially available from 3M™ ESPE™ at a weight ratio 1 to 4 (powder).

A control was made in the same manner except that HEMA was used in place of PIL H.

|  | DTS (Mpa) | Std. Dev. |
| --- | --- | --- |
| Example 17 | 47.5 | 7.2 |
| Example 18 | 48.1 | 2.83 |
| Control Restorative | 42.6 | 6.1 |

What is claimed is:

1. A curable dental composition comprising a polymerizable ionic liquid, wherein the dental composition is an adhesive, sealant or composite and the polymerizable ionic liquid is a multifunctional polymerizable liquid comprising an anion, a cation, and at least two free-radically polymerizable groups, wherein the free-radically polymerizable group is selected from (meth)acryl, vinyl, or vinyl ethers, and wherein the polymerizable ionic liquid has an air to nitrogen curing exotherm ratio of at least 0.90.

2. The curable dental composition of claim 1 wherein the polymerizable ionic liquid further comprises a monofunctional ionic liquid.

3. The curable dental composition of claim 1 further comprising at least one other ethylenically unsaturated monomer, oligomer, or polymer having an air to nitrogen curing exotherm ratio of no greater than 0.50.

4. The curable dental composition of claim 2 wherein the monofunctional polymerizable ionic liquid comprises a polymerizable cation.

5. The curable dental composition of claim 2 wherein the monofunctional polymerizable ionic liquid comprises a substituted imidazolium cationic group.

6. The curable dental composition of claim 1 wherein the polymerizable ionic liquid comprises an anion, a cationic group, and at least two ethylenically unsaturated groups bonded to the cation.

7. The curable dental composition of claim 1 wherein the polymerizable ionic liquid comprises a substituted ammonium cationic group.

8. The curable dental composition of claim 1 wherein the polymerizable ionic liquid comprises a sulfonate anion.

9. The curable dental composition of claim 1 wherein the dental composition comprises at least one photoinitiator.

10. The curable dental composition of claim 1 wherein the dental composition further comprises a filler.

11. The curable dental composition of claim 3 wherein the other ethylenically unsaturated monomer, oligomer, or polymer is present in an amount of 25 wt-% to about 65 wt-% of the total unfilled dental composition.

12. The curable dental composition of claim 1 wherein the polymerizable ionic liquid has a melting point below 25° C.

13. The curable dental composition of claim 1 wherein the polymerizable ionic liquid comprises as organic anion.

14. The curable dental composition of claim 1 wherein the polymerizable ionic liquid comprises a polymerizable anion.

15. A dental article comprising the cured composition of claim 1 wherein the dental article is a filling, crown, bridge, or restoration for an implant.

16. A method of making a dental restoration comprising: providing the curable dental composition of claim 1; forming a dental restoration from the composition; and curing the composition.

17. A method of use of a dental composition comprising: providing the curable dental composition of claim 1; applying the composition to a tooth surface; and curing the composition.

18. The curable dental composition of claim 1 wherein the polymerizable ionic liquid comprises a polymerizable aromatic cation comprising at least one free-radically polymerizable group and a polymerizable anion comprising at least one free-radically polymerizable group.

19. The polymerizable ionic liquid of claim 18 wherein the polymerizable ionic liquid has the general formula:

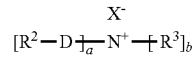

$R^3$ is independently hydrogen or a C2-C8 alkyl group;
$R^2$ is a free-radically polymerizable group;
D is a divalent linking group comprising an aromatic moiety;
a is 1-4;
b is 0-3;
a+b=4; and
$X^-$ is an organic cation comprising at least one free-radically polymerizable group.

20. The polymerizable ionic liquid of claim 18 wherein the polymerizable ionic liquid has the general formula:

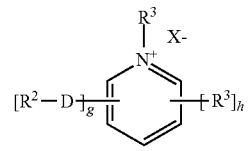

$R^3$ is independently hydrogen or a C2-C8 alkyl group;
$R^2$ is a free-radically polymerizable group;
D is a divalent linking group;
g is 1-5;
h is 0-4;
g+h=5; and
$X^-$ is an organic cation comprising at least one free-radically polymerizable group.

21. The method of claim 17 wherein the dental composition is a dental primer, dental adhesive, or dental sealant.

22. The method of claim 16 wherein the curable dental composition is cured in air.

23. The method of claim 17 wherein the curable dental composition is cured in air.

* * * * *

UNITED STATES PATENT AND TRADEMARK OFFICE
CERTIFICATE OF CORRECTION

PATENT NO. : 8,853,338 B2
APPLICATION NO. : 13/510991
DATED : October 7, 2014
INVENTOR(S) : Wang et al.

It is certified that error appears in the above-identified patent and that said Letters Patent is hereby corrected as shown below:

On the Title Page, Item (56)

Page 2, Column 2 (Other Publications)
Line 3, delete "0₂," and insert -- $O_2$, --, therefor.

Line 7, delete "Evalutaion" and insert -- Evaluation --, therefor.

Page 3, Column 1 (Other Publications)
Line 25, delete "Acryalte" and insert -- Acrylate --, therefor.

Line 54, delete "Polyer" and insert -- Polymer --, therefor.

Line 57, delete "C".

Page 3, Column 2 (Other Publications)
Line 18, delete "Boiengineering," and insert -- Bioengineering, --, therefor.

Line 19, delete "Termally" and insert -- Thermally --, therefor.

Line 36, delete "Dialkyimidazolium" and insert -- Dialkylimidazolium --, therefor.

Line 47, delete "Electrom-" and insert -- Electron- --, therefor.

In the Specification

Column 2
Line 5, delete "restorative" and insert -- restorative. --, therefor.

Signed and Sealed this
Second Day of June, 2015

Michelle K. Lee
*Director of the United States Patent and Trademark Office*

Column 2
Lines 45-46, delete "crosslinking" and insert -- crosslinking. --, therefor.

Line 59, delete "thereof" and insert -- thereof; --, therefor.

Line 61, delete "thereof" and insert -- thereof; --, therefor.

Column 3
Line 29, delete "benzthiazolyl." and insert -- benzothiazolyl. --, therefor.

Column 6
Line 36, delete "heteratoms" and insert -- heteroatoms --, therefor.

Column 13
Line 31, delete "methylheptyamine," and insert -- methylheptylamine, --, therefor.

Column 20
Line 61, delete "tetrafluoroboarate." and insert -- tetrafluoroborate. --, therefor.

Column 21
Line 23, delete "propane-1" and insert -- propan-1 --, therefor.

Line 43, delete "propane-1" and insert -- propan-1 --, therefor.

Column 28
Line 25, delete "artilces" and insert -- articles --, therefor.

Column 32
Line 67, delete "g)" and insert -- g). --, therefor.

Column 43
Line 7, (Table), delete "9" and insert -- 13 --, therefor.